US007739911B2

(12) United States Patent
Panetta

(10) Patent No.: US 7,739,911 B2
(45) Date of Patent: Jun. 22, 2010

(54) ULTRASONIC CHARACTERIZATION OF SOLID LIQUID SUSPENSIONS

(75) Inventor: Paul D. Panetta, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 194 days.

(21) Appl. No.: 11/532,484

(22) Filed: Sep. 15, 2006

(65) Prior Publication Data
US 2008/0066551 A1 Mar. 20, 2008

(51) Int. Cl.
*G01N 29/00* (2006.01)
*G01N 15/00* (2006.01)
*G01N 7/00* (2006.01)

(52) U.S. Cl. .................. 73/599; 73/865.5; 73/61.75; 73/1.83; 73/1.86

(58) Field of Classification Search ............... 73/61.75, 73/64.53, 590, 596–600, 602, 64.41, 61.71, 73/61.42, 865.5
See application file for complete search history.

(56) References Cited

U.S. PATENT DOCUMENTS

| 4,412,451 A |   | 11/1983 | Uusitalo et al. |         |
|-------------|---|---------|----------------|---------|
| 4,580,444 A | * | 4/1986  | Abts et al. ........... | 73/61.75 |
| 4,739,662 A | * | 4/1988  | Foote .................. | 73/599   |
| 4,911,013 A | * | 3/1990  | Karras et al. ......... | 73/599   |
| 5,121,629 A | * | 6/1992  | Alba .................. | 73/61.41 |
| 6,148,655 A | * | 11/2000 | Hall et al. ........... | 73/1.83  |
| 6,698,276 B2 |  | 3/2004  | Povey et al.   |         |
| 6,945,096 B1 | * | 9/2005  | Jones et al. ......... | 73/61.75 |
| 7,114,375 B2 | * | 10/2006 | Panetta et al. ....... | 73/61.75 |
| 7,140,239 B2 | * | 11/2006 | Greenwood et al. ..... | 73/61.63 |
| 2004/0060356 A1 |  | 4/2004 | Scott |         |
| 2005/0150275 A1 |  | 7/2005 | Panetta et al. |         |

FOREIGN PATENT DOCUMENTS

WO   WO 97/46159 A    12/1997

OTHER PUBLICATIONS

Allegra, J.R., and Hawley, S.A., "Attenuation of Sound in Suspensions and Emulsions: Theory and Experiments," *J. Acoust. Soc. Am.*, vol. 51, No. 5 (Part 2), pp. 1545-1564, Jul. 1972.

Challis, et al., "Equivalence between three scattering formulations for ultrasonic wave propagation in particulate mixtures," *J. Phys. D: Appl. Phys.* 31, pp. 3481-3497, 1998.

Commander, Kerry W. & Prosperetti, Andrea, "Linear pressure waves in bubbly liquids: Comparison between theory and experiments," *J. Acoust. Soc. Am.* 85 (2), pp. 732-746, Feb., 1989.

(Continued)

*Primary Examiner*—Helen C. Kwok
(74) *Attorney, Agent, or Firm*—Klarquist Sparkman, LLP

(57) ABSTRACT

Using an ultrasonic field, properties of a solid liquid suspension such as through-transmission attenuation, backscattering, and diffuse field are measured. These properties are converted to quantities indicating the strength of different loss mechanisms (such as absorption, single scattering and multiple scattering) among particles in the suspension. Such separation of the loss mechanisms can allow for direct comparison of the attenuating effects of the mechanisms. These comparisons can also indicate a model most likely to accurately characterize the suspension and can aid in determination of properties such as particle size, concentration, and density of the suspension.

30 Claims, 17 Drawing Sheets

OTHER PUBLICATIONS

Crawford, A.M., and Hay, Alex E., "Determining suspended sand size and concentration from multifrequency acoustic backscatter," *J. Acoust. Soc. Am.*, 94 (6), pp. 3312-3324, Dec. 1993.

Davis, M.C., "Attenuation of sound in highly concentrated suspensions and emulsions," *J. Acoust. Soc. Am.* 65 (2), pp. 387-390, Feb. 1979.

De Rosny, Julien, and Roux, Philippe, "Multiple scattering in a reflecting cavity: Application to fish counting in a tank," *J. Acoust. Soc. Am*, 109 (6), pp. 2587-2597, Jun. 2001.

De Rosny, Julien, and Roux, Philippe, Reply to the Comment on "Multiple scattering in a reflecting cavity: Application to fish counting in a tak" [J. Acoust. Soc. Am., 113, 2978-2979(2003)], *J. Acoust. Soc. Am.* 115(1), pp. 31-34, Jan. 2004.

Dukhin, Andrei S., and Goetz, Philip J., "Characterization of chemical polishing materials (monomodal and bimodal) by means of acoustic spectroscopy,"*Colloids and Surfaces A*, 158, pp. 343-354. 1999.

Egle, Davis M., "Diffuse wave fields in solid media," *J. Acoust. Soc. Am.* 70 (2), pp. 476-480, Aug. 1981.

Georgiou, Georgia, "Statistical Characterization of Diffuse Scattering in Ultrasound Images," *IEEE Transacations on Ultrasonics, Ferroelectrics, and Frequency Control*, vol. 45, No. 1, pp. 57-64, January 1998.

Goebbels, K., "Structure Analysis by Scattered Ultrasonic Radiation," *Research Techniques in Nondestructive Testing*, vol. IV, (edited by R.S.Sharpe), Academic Press, New York, pp. 86-157, 1980.

Han, Y.K., and Thompson, R.B., "Ultrasonic Backscattering in Duplex Microstructures: Theory and Application to Titanium Alloys," *Metallurgical and Materials Transactions*, vol. 28A, pp. 91-103, Jan. 1997.

Keller, Joseph B., "Stochastic Equations and Wave Propagation in Random Media," *Proceedings of the 16$^{th}$ Symposium on Applied Mathematics, American Mathematics Society*, New York, New York, pp. 145-170, 1964.

Panetta et al., "Characterization of solid liquid suspensions utilizing ultrasonic measurements," *Review of Quantitative Nondestructive Evaluation*, vol. 22, ed. by D.O. Thompson and D.E. Chimenti, pp. 1644-1650, 2003.

Panetta et al., "Characterization of solid liquid suspensions utilizing non-invasive ultrasonic measurements," *Symposia Papers Presented Before the Division of Environmental Chemistry*, American Chemical Society, Anaheim, CA, pp. 527-534, Mar. 28-Apr. 1, 2004.

Schmerr, Lester W., Jr., "Diffraction Correction Inegral," *Fundamentals of Ultrasonic Nondestructive Evaluation, A Modeling Approach*, New York, Plenum Press, pp. 289-295, 1998.

Scott, David M., "Ten Years of Industrial Applications of In-Line Ultrasonic Spectroscopy," *Particulate Systems Analysis*, Harrogate, UK, 2003.

Scott, et al., "In-Line Particle Characterization," *Part. Syst. Charact.* 15, pp. 47-50, 1998.

Scott, et al., "Ultrasonic Measurements of Sub-Micron Particles," *Part. Syst. Charact,*, 12 pp. 269-273, 1995.

Soong, et al., "Ultrasonic Characterization of Three-Phase Slurries," *Chem. Eng. Comm.* vol. 138, pp. 213-224, OPA, Amsterdam, B.V., 1995.

Spelt, et al., "Attenuation of sound in concentrated suspensions: theory and experiments," *J. Fluid Mech.*, vol. 430, pp. 51-86, Cambridge University Press, UK, 2001.

Spelt, et al., "Determination of particle size distributions from acoustic wave propagation measurements," *Physics of Fluids*, vol. 11, No. 5, pp. 1065-1080, May 1999.

Stanke, Fred E., "Inversion of Attenuation Measurements in Terms of a Parameterized Autocorrelation Function," *NDE of Microstructure for Process Control* (editor: H.N.G. Wadley), pp. 55-60, American Society for Metals, 1985.

Stanke, Fred E., and Kino, G.S., "A unified theory for elastic wave propagation in polycrystalline materials," *J. Acoust. Soc. Am.* 75 (3), pp. 665-681, Mar. 1984.

Thompson, R.B., and Gray, T.A., "A model relating ultrasonic scattering measurements through liquid-solid interfaces to unbounded medium scattering amplitudes,", *J. Acoust. Soc. Am.*, 74 (4), pp. 1279-1290, Oct. 1983.

Thompson, R.B., and Gray, T.A., Erratum: A model relating ultrasonic scattering measurements through liquid-solid interfaces to unbounded medium scattering amplitudes [J. Acoust Soc. Am. 74, 1279-1290 (1983)], *J. Acoust. Soc. Am* 75 (5), May 1984.

Thorn, Peter D., and Hardcastle, Peter J., "Acoustic measurements of suspended sediments in turbulent currents and comparison with in-situ samples," *J. Acoust. Soc. Am.* 101 (5), Pt. 1, pp. 2603-2614, May 1997.

Waterman, P.C., and Truell, Rohn, "Multiple Scattering of Waves," *Journal of Mathematical Physics*, vol. 2, No. 4, Jul.-Aug. 1961.

Watson, Kenneth M., "Multiple Scattering of Electromagnetic Waves in an Underdense Plasma," *Journal of mathematical Physics*, vol. 10, No. 4, pp. 688-702, Apr. 1969.

Weaver, et al., "Diffuse Ultrasound in Polycrystalline Solids," *Ultrasonics International '91 Conference Proceedings*, pp. 507-510, 1991.

Weaver, R.L., "Anderson Localization of Ultrasound," *Wave Motion*, 12, pp. 129-142, Elsevier Sience Publishers B.V., North-Holland, 1990.

Weaver, Richard L. and Sachse, Wolfgang, "Diffusion of ultrasound in a glass bead slurry," *J. Acoust. Soc. Am.*, 97 (4), pp. 2094-2102, Apr. 1995.

Weaver, Richard L., "Diffuse Field Decay Rates for Material Characterization," *Solid Mechanics Research for Quantitative Nondestructive Evaluation* (editors: J.D. Achenbach and Y. Rajapakse), pp. 425-434, 1987.

Allegra et al., "Attenuation of Sound in Suspensions and Emulsions: Theory and Experiments," *Journal of the Acoustical Society of America*, vol. 51, No. 5, Part 2, pp. 1545-1564 (May 1972).

Kytomaa, H.K., "Theory of Sound Propagation in Suspensions: A Guide to Particle Size and Concentration Characterization," *Powder Technology*, vol. 82, pp. 115-121 (1995).

Invitation to Pay Additional Fees and Communication Relating to the Results of the Partial International Search in International Application No. PCT/US2007/078246, Mar. 20, 2008.

International Search Report, mailed Jul. 1, 2008, in International Application No. PCT/US2007/078246, filed Sep. 12, 2007.

Written Opinion of the International Searching Authority, mailed Jul. 1, 2008, in International Application No. PCT/US2007/078246, filed Sep. 12, 2007.

* cited by examiner

ULTRASONIC CHARACTERIZATION OF SOLID LIQUID SUSPENSIONS

ACKNOWLEDGMENT OF GOVERNMENT SUPPORT

The disclosed technologies were made with Government support under Contract DE-AC05-76RLO1830 awarded by the U.S. Department of Energy. The Government has certain rights in the technologies.

FIELD

The technologies disclosed herein are generally related to characterizing properties of solid liquid suspensions using ultrasonic measurements.

BACKGROUND

Suspensions or slurries having moderate and high particle concentrations are found in a variety of industries. As the characteristics of the suspensions influence production costs, product quality and yield, it is useful to rapidly, cost-effectively, and non-invasively characterize these suspensions.

Commercially available devices utilizing ultrasonic measurements for particle sizing typically rely on a measurement of the through-transmitted attenuation and the velocity. While effective at low solid concentrations (<10 wt %), particle-particle interactions in higher concentration slurries can complicate both the measurement and the interpretation of the data. Also, it may be difficult to tell at what point a given measurement (e.g., through-transmission attenuation) becomes unreliable. Another potential problem arises from the very small propagation paths (on the order of millimeters), found in some commercial devices, which can become clogged. Additionally, such measurements are often obtained using facing transducers, which can lead to inaccuracies from misaligned transducers.

SUMMARY

Measuring the ultrasonic properties of through-transmission attenuation, backscattering, and diffuse field can indicate the strength of different loss mechanisms (such as absorption, single scattering, multiple scattering, and particle-particle interactions) among particles in a solid-liquid suspension. (In the context of this application, "solid-liquid suspension" includes "emulsion.") Attenuation mechanisms can be separated for direct comparison. Comparing measurements of two or more mechanisms can indicate the model most likely to accurately characterize the suspension and can aid in determination of particle size, concentration, and density of slurries. The characterizations may be accomplished without diluting the slurry.

In one embodiment, a method of characterizing a solid liquid suspension includes obtaining two or more property measurements for the suspension using an ultrasonic field, converting the property measurements to comparable quantities, and determining one or more dominant loss mechanisms for the suspension according to the comparable quantities. The method can also include selecting a model according to the determination of one or more loss mechanisms, and determining one or more characteristics of the suspension (e.g., determining particle size, concentration, and/or density) by evaluating one or more of the property measurements according to the selected model. Loss mechanism terms can include multiple scattering (including particle-particle interactions), single scattering, and absorption. Converting the property measurements can also include determining the attenuation of one or more of the property measurements and calculating an attenuation due to a loss mechanism. If the loss mechanism is multiple scattering, the attenuation due to multiple scattering can be calculated as a difference of an attenuation of a through-transmitted signal and an attenuation of a backscattered signal. If the loss mechanism is single scattering, the attenuation due to single scattering can be calculated as a difference of an attenuation of a backscattered signal and an attenuation of a diffuse field signal. If the loss mechanism is absorption, the attenuation due to absorption can be calculated as equal to an attenuation of a diffuse field signal. The attenuation of a backscattered signal can be calculated as a function of the frequency of the ultrasonic signal, a decay rate function for the backscattered signal, and the speed of sound in the suspension. The attenuation of a diffuse field signal can be calculated as a function of the frequency of the ultrasonic signal, a decay rate function for the diffuse field signal, and the speed of sound in the suspension. The suspensions being measured can have solid concentrations greater than about 10 wt %, 20 wt %, 30 wt %, 40 wt %, 50 wt % or more. A computer-readable medium can contain instructions which can cause a computer to execute the method and store the results in a computer-readable medium.

In another embodiment, converting the measurements to comparable quantities can include calculating a degree of energy loss for the measurements. A degree of energy loss for through-transmission attenuation measurement can be calculated as a function the frequency of the ultrasonic field and the through-transmitted attenuation. A degree of energy loss for backscattering measurement can be calculated as a function of the frequency of the ultrasonic field. A degree of energy loss for the diffuse field measurement can be calculated as a function of the frequency of the ultrasonic field.

In a further embodiment, a system for characterizing a solid-liquid suspension includes an ultrasonic measurement device and a computer configured to perform a method. The method can include: receiving from the measurement device two or more property measurements for the suspension; converting the property measurements to comparable quantities; determining one or more dominant loss mechanisms for the suspension according to the comparable quantities; selecting a model according to a result of the comparison; and determining one or more characteristics of the suspension by evaluating one or more of the property measurements according to the selected model. The system can also include an output device for displaying one or more results related to the method and can also include an input device for receiving one or more parameters related to the method.

In another embodiment, an ultrasonic measurement device includes a container for holding a sample and exactly one planar transducer, wherein the transducer is configured to transmit an ultrasonic signal into the sample, and wherein the transducer is configured to measure the decay of backscattered energy in a given section of the container.

Ultrasonic characterization of solid-liquid suspensions has applications in a number of industries, including: pharmaceutical, chemical, mining, waste removal, pollution control, nuclear energy, and most other industries that process solid-liquid suspensions.

This Summary is provided to introduce a selection of concepts in a simplified form that are further described below in the Detailed Description. This Summary is not intended to identify key features or essential features of the claimed subject matter, nor is it intended to be used as an aid in determin-

DETAILED DESCRIPTION

Ultrasonic-Slurry Interactions

Figure 1:
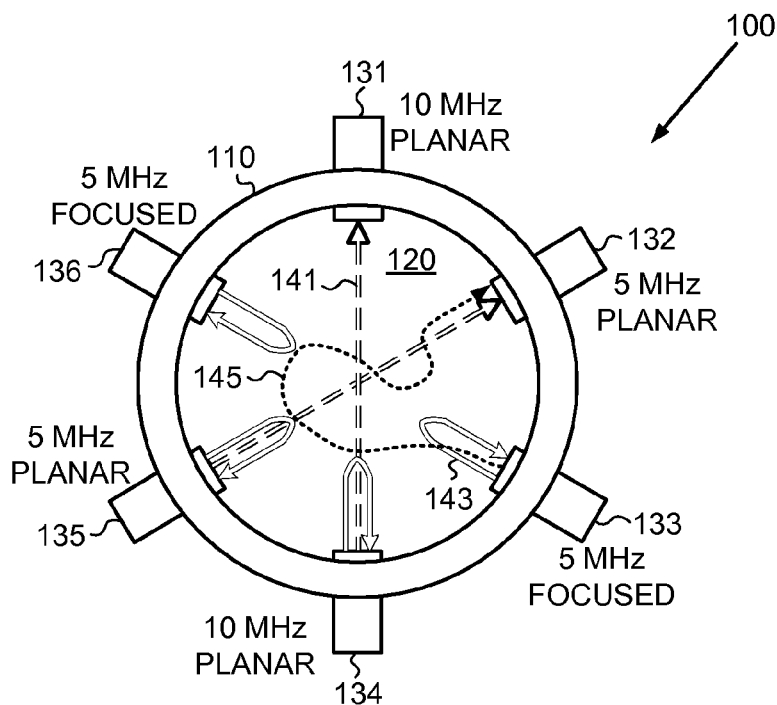
FIG. 1A is a top diagrammatic view of a container and transducer array for performing ultrasonic backscattering, through-transmission attenuation, and velocity measurements on suspensions.
FIG. 1B is a top diagrammatic view of a container and transducer for performing ultrasonic backscattering measurements on suspensions.

As an ultrasonic field moves through a slurry, the fluid and the solids interact with the ultrasonic field in several ways, causing the field to lose energy. For example, the ultrasonic field can be scattered at the interfaces between the particle and the fluid. Additionally, energy can be lost through heat generated by friction as the particle is moved through the viscous fluid. Changing the direction of motion of the particle as it oscillates (i.e., accelerating and decelerating the particle) also removes energy from the ultrasonic field. If the particle is not rigid, then it can also change shape as the ultrasonic field moves through the media, causing additional energy loss. Furthermore, the oscillatory nature of the ultrasonic field can cause additional pressure gradients between the nodes and antinodes of the field, creating a small temperature gradient, which causes heat flow and additional energy loss. These loss mechanisms can be broadly categorized as scattering losses and as damping or absorption losses. While there are many contributions to energy loss as the ultrasonic field interacts with the fluid and the solid phases of the slurry, the dominant contributions are (1) the heat loss due to the friction between the viscous fluid and the particles as they move through the slurry, (2) the energy required to accelerate and decelerate the particle as it oscillates, and (3) the scattering of sound out of the propagating field.

Several properties of an ultrasonic field are affected by characteristics of the medium in which the field propagates. These properties, which are discussed below, include through-transmission attenuation, backscattering, velocity, and diffuse field strength.

Through-Transmission Attenuation

Ultrasonic fields propagating in suspensions can suffer attenuation due to viscous, thermal, and scattering mechanisms. Through-transmission attenuation has been used widely and successfully to characterize dilute slurries. One model accounts for the through-transmission attenuation due to viscous damping. According to this model, as a particle in a slurry moves and changes shape in response to the ultrasonic field, energy is lost as heat exchanged between the field and the particle. An additional energy loss occurs as the propagating wave is scattered at the interfaces between the fluid and the solid particles. Research in the field has shown that at high concentrations, multiple scattering and particle-particle interactions are significant contributions to through-transmitted attenuation, and models need to be developed to make methods which rely on the through transmitted attenuation functional at higher concentrations.

The main obstacles to implementing through-transmission attenuation measurements to slurry characterization are usually the mathematical complexities of accounting for multiple scattering at high concentrations, as well as the accompanying complex nature of the inversion process. Additionally, the through-transmission attenuation measurement often requires careful alignment of transducers, the use of a reference signal to correct for transducer efficiency, and a correction for diffraction effects on the amplitude. These issues further decrease the accuracy and precision of the methodologies based on through-transmission attenuation alone.

Backscattering

An ultrasonic backscattering measurement can be attractive because viscous, thermal, and inertial effects generally have small contributions to backscattering. Furthermore, backscattering theories are often less complicated than through-transmission attenuation theories and lend themselves to more stable inversion processes. Moreover, since the measurements of backscattering and diffuse fields usually do not require long travel distances of the ultrasound signal through the slurry, they may be performed in moderately or highly concentrated slurries and with a single transducer so as to avoid the alignment and stability problems of transducer pairs. Additionally, a backscattering amplitude taken in a fixed time increment is expected to be dominated by the scattering effects of the slurry, with lesser contributions from the viscous and thermal losses.

Backscattering measurements utilizing a single transducer can have several advantages over through-transmission attenuation measurements, including: insensitivity to diffraction and alignment of the transducer; transducer efficiency; and small propagation distances. These features can make them useful for characterizing highly attenuating slurries. Additionally, since the direct backscattered field can usually be described by single-scattering processes, the mathematical inversion processes is often simpler and more stable than those used for through-transmission attenuation. Backscattering can also offer the ability to determine the spatial distribution of the slurry properties and to probe for inhomogeneities. Backscattering in slurries and suspensions has been less thoroughly studied, relative to through-transmission attenuation, with the efforts focused on geologic and oceanographic applications. Research has characterized the backscattering amplitude as a function of the elastic properties of the scatterers and the viscous fluid.

Diffuse Field

Another aspect of the scattered field that is related to the properties of the scattering media is the portion that undergoes multiple scattering and for which propagation can be described by a diffusion process. In elastic solids and slurries, these signals can arrive at the transducer after several milliseconds, as compared to the direct backscattered field, for which the signals typically arrive in several microseconds. After multiple scattering events, the ultrasonic diffuse field develops, and a portion of the scattered wave is eventually returned to the transducer. Buildup of the diffuse field is governed by a diffusivity term that is a function of the mean free path and, thus, is related to the size of the scatterers. The decay is related to the energy absorbed from the ultrasonic field.

It is commonly believed that the energy loss of the diffuse field is due to damping mechanisms (e.g., viscous losses) and does not contain contributions from scattering losses. This parameter can therefore offer the opportunity to probe only the damping mechanisms.

Velocity

Velocity measurements are often useful for characterizing ultrasonic fields. However, because measurement of this property is relatively straightforward and is well known in the art, it is not elaborated here.

Table 1 summarizes the predominant energy loss mechanisms for each measurement property.

TABLE 1

| Measurement Property | Loss Mechanism |
| --- | --- |
| Through-transmission attenuation | Absorption (viscous, particle acceleration), single scattering, multiple scattering (including particle—particle interactions) |
| Backscatter | Absorption (viscous, particle acceleration), single scattering |
| Diffuse field | Absorption (viscous, particle acceleration) |

Example Measurement Apparatus and Measurements

FIG. 1A shows a top diagrammatic view of a system 100 for measuring ultrasonic backscattering, through-transmission attenuation, and velocity measurements on suspensions. The system 100 comprises a cylindrical container 110 which holds a suspension 120. Transducers 131-136 are arranged in opposing pairs (i.e., 131 and 134, 132 and 135, 133 and 136), and the transducers 131-136 may be planar or focused. In this system, through-transmission attenuation and velocity are determined according to signals that traverse the container and are received by the transducer on the opposite side of the container. For example, transducer 134 transmits a 10 MHz ultrasonic wave through suspension 120 to transducer 131, as indicated by broken arrow 141. Backscattering is determined by measuring a sound wave which is scattered back to the transmitting transducer. For example, transducer 133 transmits an ultrasonic wave (shown by arrow 143) which is reflected back to transducer 133. A related property, off-axis scattering (not shown in FIG. 1), occurs when sound travels from a transducer and is reflected by particles in the suspension into a neighboring transducer. A diffuse field (shown by broken arrow 145) can be determined by measuring sound that travels from a first transducer (e.g., transducer 133), is scattered by multiple particles in the suspension 120, and is then received by the same transmitting transducer or a second transducer (e.g., transducer 132).

Transducers 131-136 may be configured to emit and receive ultrasonic waves of differing frequencies. For example, transducers 132, 135, 136 are configured to transmit and receive 5 MHz signals. Those of skill in the art will recognize other appropriate frequencies for various situations.

In one embodiment of the system 100 of FIG. 1, the container 110 was comprised of Teflon, and typical properties of the transducers were as shown in Table 2. A pulser, such as the Ritec SP-801 from Ritec, Inc., was used to excite the transducers and a Ritec BR-640 receiver was used to amplify and filter received signals. The pulser was set to optimally excite the transducers with a square wave pulse dependent on the nominal transducer frequency response. The receiver gain was typically set to 64 dB for backscatter measurements and varied between −8 dB and 52 dB for through-transmission attenuation measurements. An input impedance of 50 Ohms was used with a bandpass filter passing frequencies between 1 and 12 MHz. For pulse-echo applications, a Ritec RDX-2 was used with a damping of 1300 Ohms and a low frequency cutoff of 1.6 MHz. Signals were captured at a sampling rate of 100 MHz, with a LeCroy 9310M oscilloscope and stored digitally on a computer via a GPIB communications port utilizing a Labview data acquisition program from National Instruments, Inc. For pitch-catch velocity and through-transmission attenuation measurements, 50 ultrasonic waveforms were averaged for each weight percentage. This signal was used to measure transit time (time to highest positive peak) and through-transmission attenuation relative to water. The Fourier amplitude of each averaged signal was calculated ($\Gamma_s(f)$), and compared with a baseline Fourier amplitude from water ($\Gamma_{ref}(f)$), to calculate the through-transmission attenuation as a function of frequency, $\alpha(f)$, using the following expression:

$$\alpha(f) = \frac{1}{z}\ln\left[\frac{D_s}{D_{ref}}\frac{\beta(f)\Gamma_{ref}(f)}{\beta(f)\Gamma_s(f)}\right] \quad (1)$$

See, e.g., Thompson et al., "A model relating ultrasonic scattering measurements through liquid-solid interfaces to unbounded medium scattering amplitudes," *J. of the Acoust. Soc. of Am.*, 74:1279-1290, October 1983. In Equation 1, z is the through-transmission distance, $D_s$ and $D_{ref}$ are the beam diffraction corrections for sample and water reference, respectively, and $\beta(f)$ is the transducer efficiency. A comparison with a reference signal in water was performed to distinguish the through-transmission attenuation in the slurry from contributions due to beam diffraction and transducer efficiency. For these samples, the diffraction correction was assumed to be the same for both the slurries and the water reference. This assumption is good considering that the speed of sound differed from water by approximately 2 or 3%. In some embodiments, the correction for the transducer efficiency can be generated from various beam models. See, e.g.: Rogers et al., "An exact expression for the Lommel diffraction correction integral," *J. of the Acoust. Soc. of Am.*, 55(4): 724-728, April 1974; and Schmerr, Section 9.2.1, "Diffraction Correction Integral," *Fundamentals of Ultrasonic Nondestructive Evaluation: A Modeling Approach*, New York, Plenum Press, 1998, pp. 289-295. For quantitative measurements of through-transmission attenuation it is important that this operation be performed to ensure that the measurements are affected only by the slurry properties.

TABLE 2

| Transducer Type | Frequency (MHz) | Focal Length (cm) |
|---|---|---|
| Focused | 5 | 0.79 |
|  | 10 | 0.60 |
| Planar | 5 | N/A |
|  | 10 | N/A |

Figure 3A:
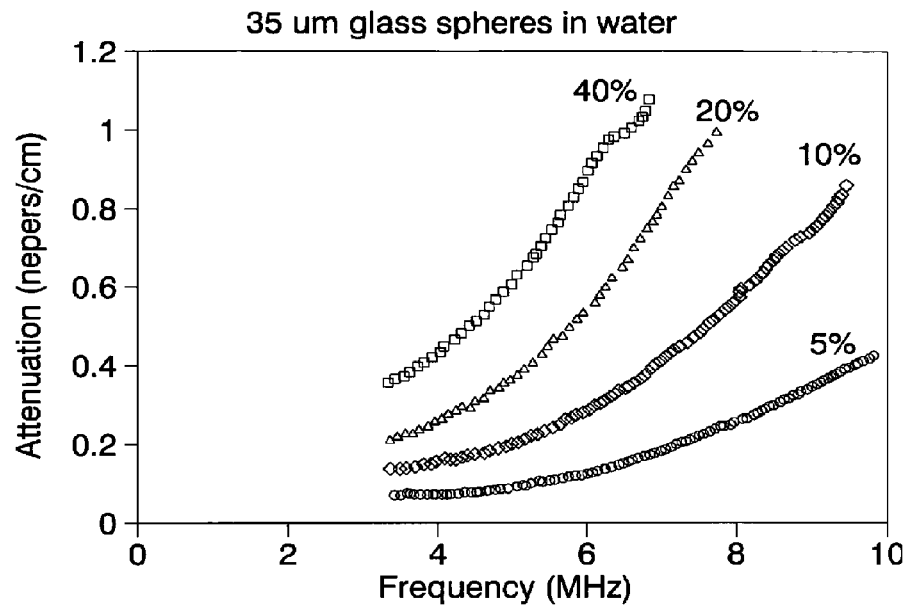
FIG. 3A is a representative plot of through-transmission attenuation versus frequency for 35 μm glass spheres in water at 5, 10, 15, 20, 30 and 40 wt %.
Figure 3B:
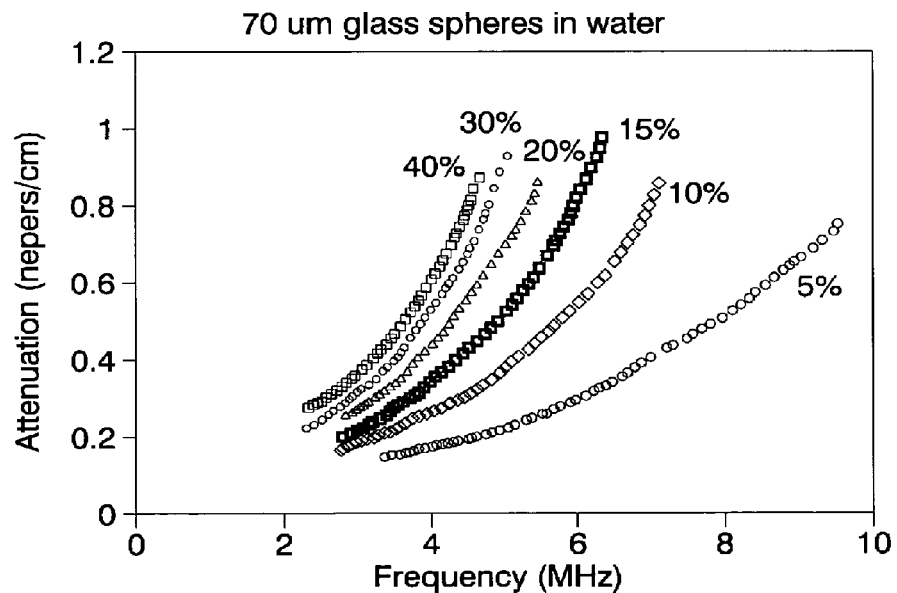
FIG. 3B is a representative plot of through-transmission attenuation versus frequency for 70 μm glass spheres in water at 5, 10, 15, 20, 30 and 40 wt %.

Results of the through-transmission attenuation in slurries comprising 35 µm and 70 µm diameter glass spheres in water are shown in FIGS. 3A and 3B, respectively, where the through-transmission attenuation as a function of frequency was calculated from the above equation. The various lines in each graph represent measurements taken from slurries at different wt % amounts, as labeled in the graphs.

Measurements of the frequency dependence of through-transmission attenuation can be employed to provide an indication of the scattering regime of the suspension. Through-transmission attenuation generally depends on the frequency $f$, the particle radius R, and the viscosity of the fluid $\mu$. The constant $k=2\pi f/v$ is often used in describing frequency dependence, where $v$ is the speed of sound. The frequency dependence is classified in three specific regimes: the viscous regime (kR<<1), the inertial damping regime (kR~1) and the multiple scattering regime (kR>>1). In the viscous regime, the through-transmission attenuation is proportional to $f^2R^2/\mu$; in the inertial damping regime, it is proportional to $(\mu f)^{1/2}/R$; and in the multiple scattering regime, it is proportional to $f^4$.

For the slurries described by FIGS. 3A and 3B, kR~1. For a 10 MHz ultrasonic field, kR is 0.7 for the 35 µm diameter particles and 1.4 for the 70 µm diameter particles. A power law, $\alpha(f)=Af^P$, can be fitted to the attenuation as a function of the signal frequency $f$ to determine the power P, where A is the amplitude of the signal. The through-transmission attenuation increases with frequency with a characteristic power P of 2.5 for the 70 µm size particles and in the range of 1.7 to 2.4 for the 35 um size particles. Considering that the kR values are ~1, this power-law frequency dependence is reasonable since the through-transmission attenuation is between the inertial and multiple scattering regimes, where the through-transmission attenuation is expected to have a frequency dependence of $f^{1/2}$ and $f^4$ respectively, as explained above.

Figure 4A:
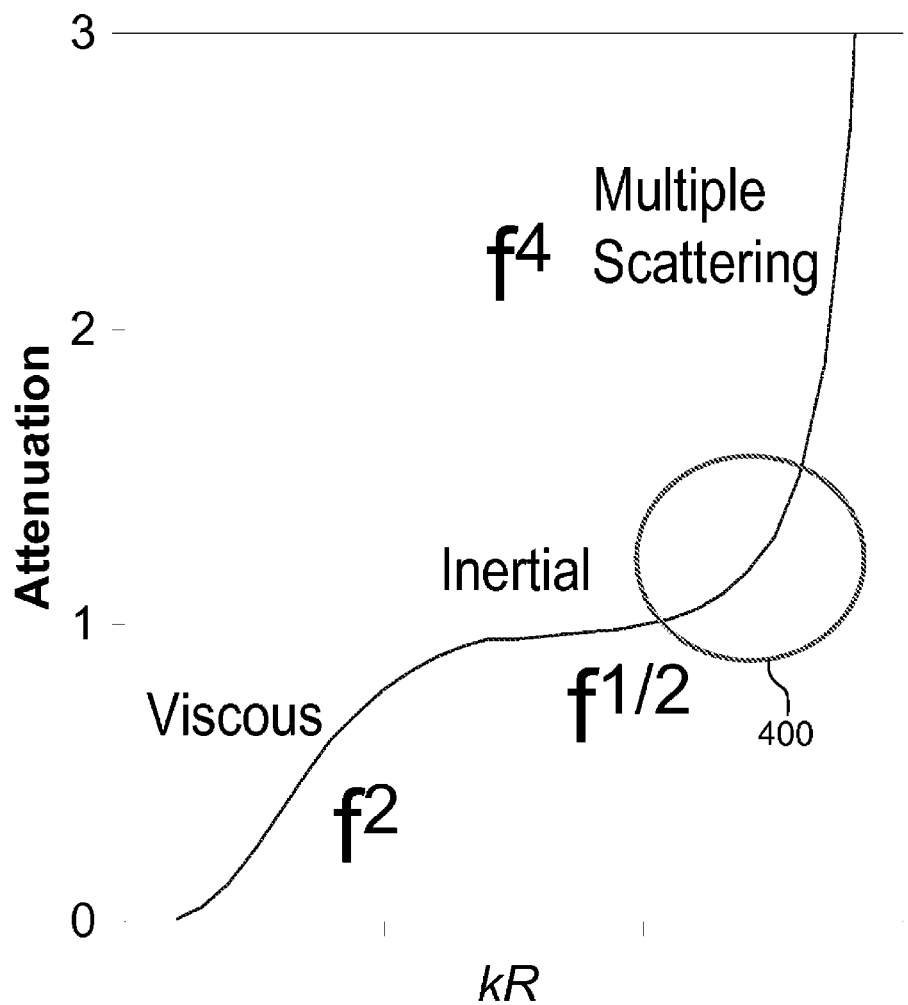
FIG. 4A is an exemplary graph of signal attenuation in three frequency-dependent regimes.
Figure 4B:
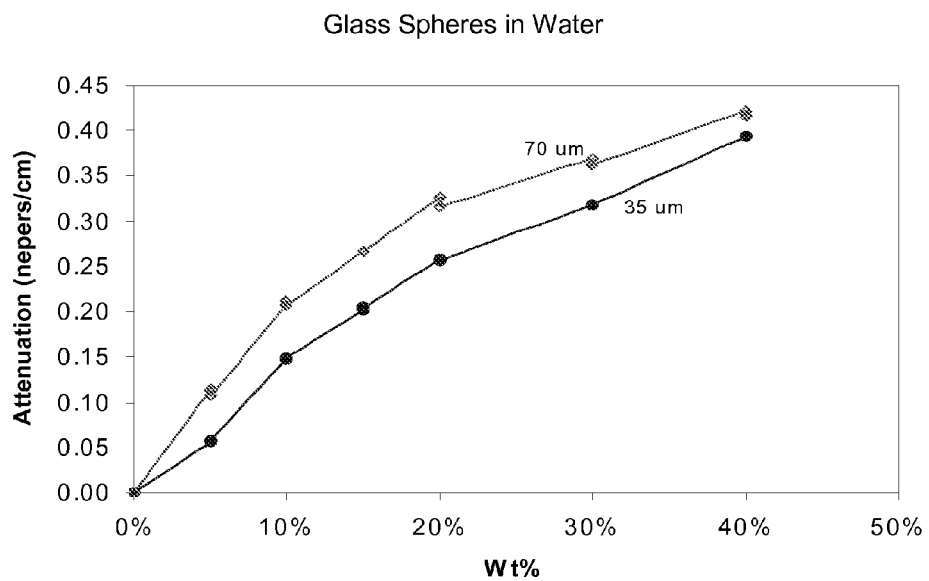
FIG. 4B is a representative graph of the through-transmission attenuation at a fixed frequency and as a function of concentrations.

An exemplary schematic of the attenuation as a function of kR is shown in FIG. 4A. The circle 400 indicates the region in kR-space where the dominant attenuation regime changes from inertial damping toward multiple scattering. As shown in FIG. 4B, the through-transmission attenuation, at a fixed frequency and as a function of concentrations, is seen to increase in a linear fashion up to approximately 10 wt % and then flatten. This nonlinear response is an indication of the increased importance of the particle-particle interactions and multiple scattering at higher concentrations. While these results are encouraging, methodologies that rely on the through-transmission attenuation still fail at high concentration.

Figure 5:
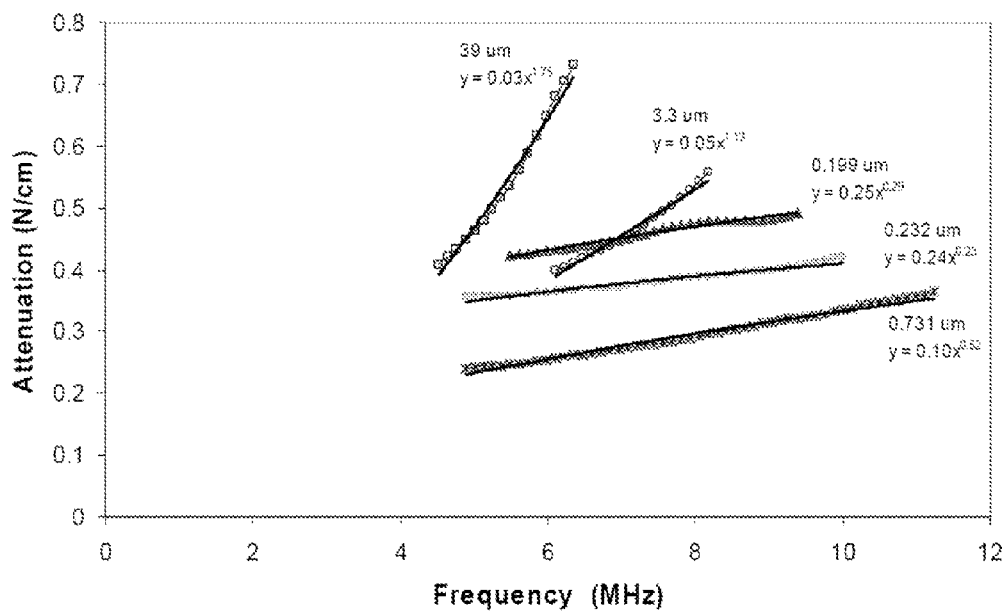
FIG. 5 is a representative plot of the through-transmission attenuation as a function of frequency on an active pharmaceutical ingredient with average particle size ranging from 0.199 μm to 39 μm.
Figure 6A:
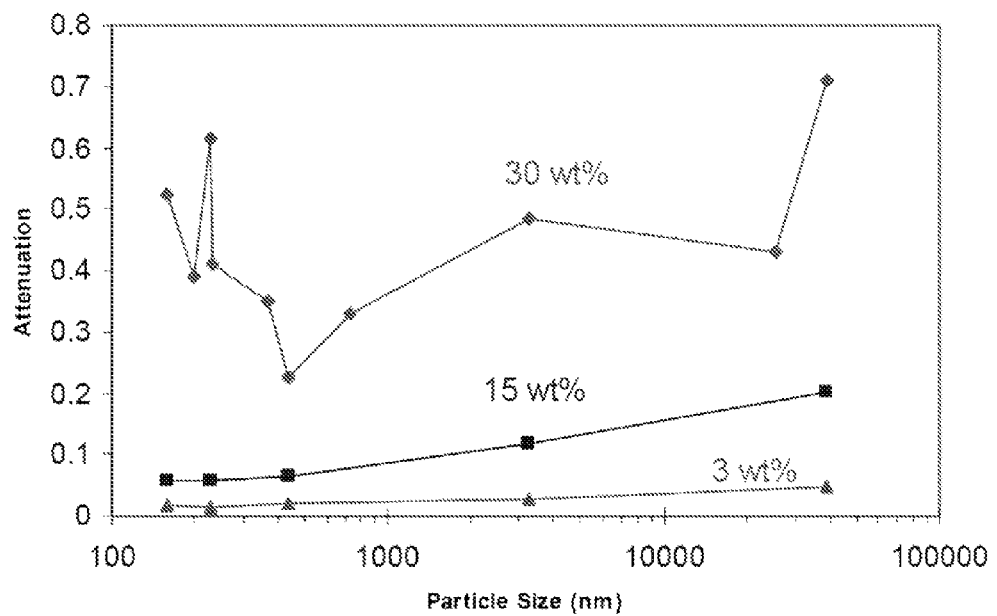
FIG. 6A is a representative plot of the through-transmission attenuation at 6 MHz for suspensions of varying particle size at concentrations of 3, 15 and 30 wt %.

FIG. 5 shows the through-transmission attenuation as a function of frequency on an active pharmaceutical ingredient with average particle size ranging from 0.199 µm to 39 µm. Clearly, there are different dependencies on frequency as the mean particle size decreased from 39 µm to 0.199 µm (a decrease in kR from 0.58 to 0.003 at 7 MHz). Solid lines in FIG. 5 are the power law fits for the equations (generated using the power law described above) shown under each particle size. To demonstrate the effects of concentration on the through-transmission attenuation, the attenuation at 6 MHz was plotted as a function of particle size, as shown in FIG. 6A. It can be seen that the attenuation at low concentration (e.g., 3 wt %) scales relatively well with particle size, however, the attenuation at 30 wt % is not monotonic with particle size. This type of non-monotonic behavior of attenuation relative to particle size implies that the particle-particle interactions and multiple scattering may be controlling the attenuation at higher concentrations. This is a further indication that methodologies that rely on through-transmission attenuation can become inaccurate at higher concentrations.

Figure 7A:
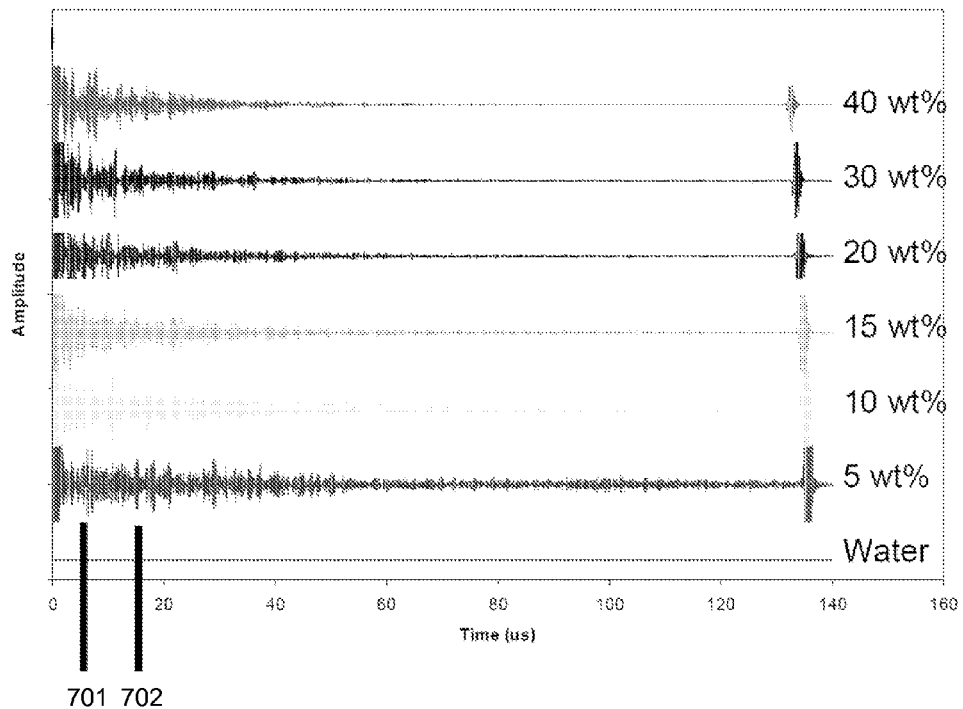
FIG. 7A is a plot of representative backscattering signals for suspensions of 5, 10, 15, 20, 30 and 40 wt %.
Figure 7B:
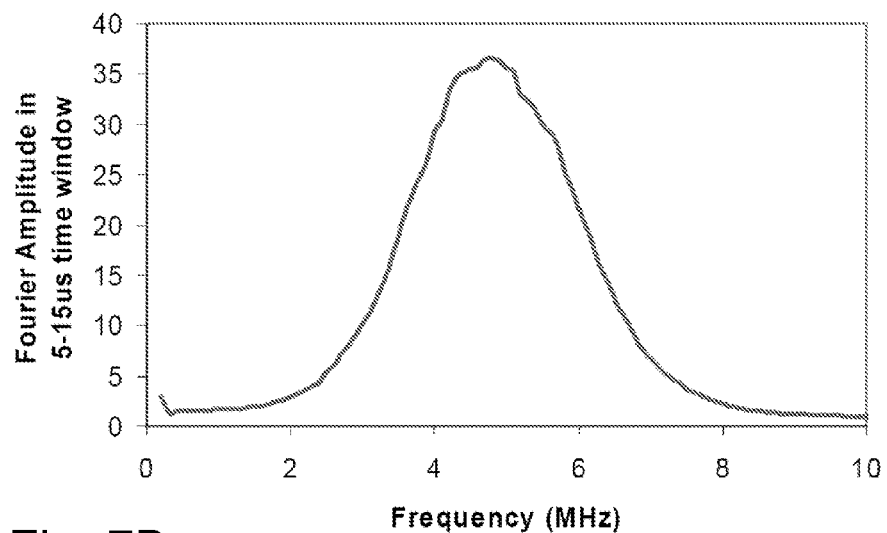
FIG. 7B is a plot of the Fourier amplitude of the backscattering signal of the 40 wt % slurry of FIG. 7A in the 5 to 15 μs region.

In one implementation, backscattering measurements were obtained by capturing 100 single-shot waveforms at multiple slurry concentrations, including pure water. Representative backscattering signals from the slurries of glass spheres are shown in FIG. 7A for the 70 µm glass spheres utilizing a 5 MHz planar transducer. The Fourier amplitude at each frequency was then averaged for all 100 waveforms. A representative Fourier amplitude of the backscattering of the 40 wt % slurry in the 5 to 15 µs region (i.e., the region indicated by markers 701, 702 in FIG. 7A) is shown as FIG. 7B.

Figure 8A:
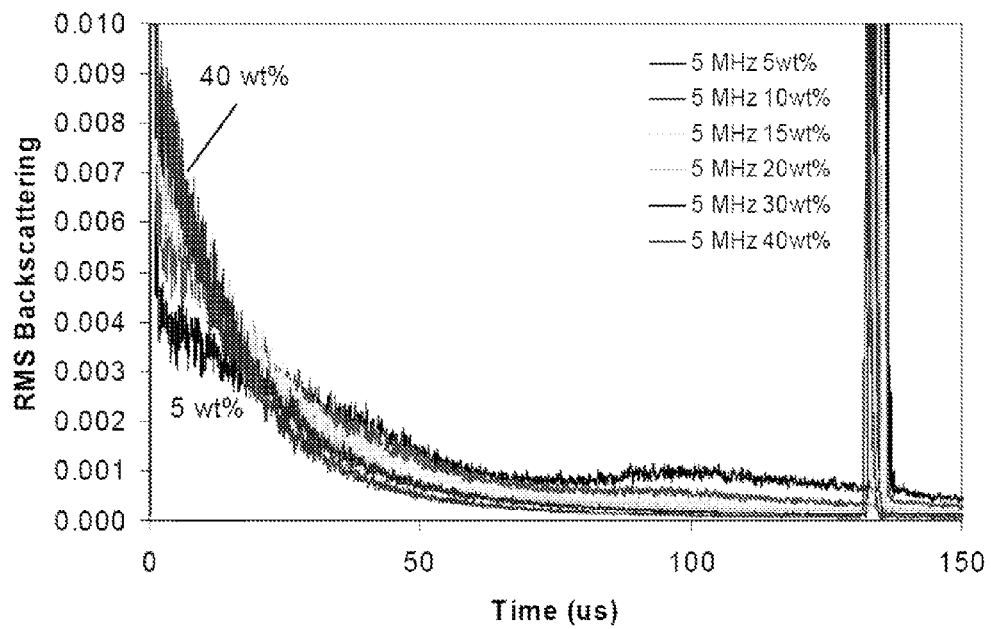
FIG. 8A is a plot of representative RMS backscattering signals at various suspension concentrations.
Figure 8B:
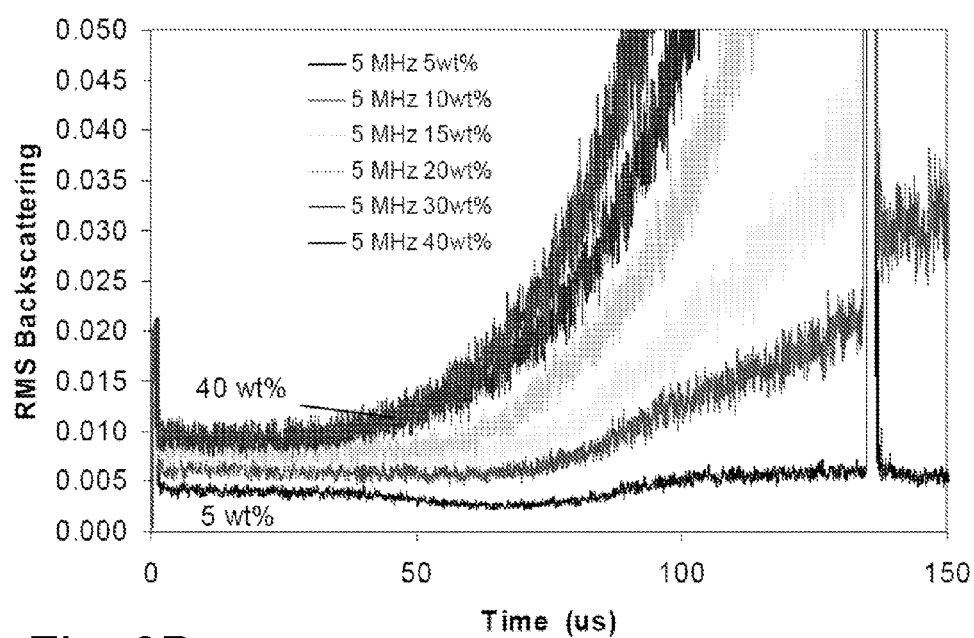
FIG. 8B is a plot of the signals of FIG. 8A multiplied by $e^{\alpha vt}$.

Several features are evident, including the amplitude and the duration of the backscattering. Specifically, the duration of the backscattering is longer for the lower concentration materials. This is due to the lower attenuation relative to the higher concentration slurries. In addition, there is an apparent decay in the amplitude in with time. This exponential decay can be used to further elucidate the mechanisms contributing to the properties of the backscattered ultrasonic field. The exponential decay is evident in the RMS backscattering as a function of time as shown in FIG. 8A for the 70 μm size particles. Two regimes are distinguishable: the time before approximately 25 μs, where the backscattering for the 40 wt % suspension is highest, and the time after 25 μs where the backscattering for the 40 wt % suspension is lowest. This behavior is understandable when considering that the traveling ultrasonic field loses energy as described above and that the attenuation of the 40 wt % suspensions is higher than the attenuation of the lower concentration suspensions. The attenuation causes a diminution of the backscattered signals by a factor of $e^{-\alpha v t}$, where $\alpha$ is the frequency dependant attenuation, $v$ is the speed of sound, and $t$ is the time. In this particular implementation, this measure of the backscattering was corrected for the attenuation in the following manner. Each backscattering attenuation spectrum shown in FIG. 8A above was fit with a power law function within the frequency bandwidth of the transducer. This power law was then used to correct the backscattering signal by multiplying the RMS backscattering by $e^{\alpha v t}$. The results of this correction are shown as FIG. 8B, showing that the backscattering increases with concentration for all time as expected. The spikes at ~135 μs in FIGS. 7A, 8A and 8B indicate reflections off of the far side of the container.

Figure 9A:
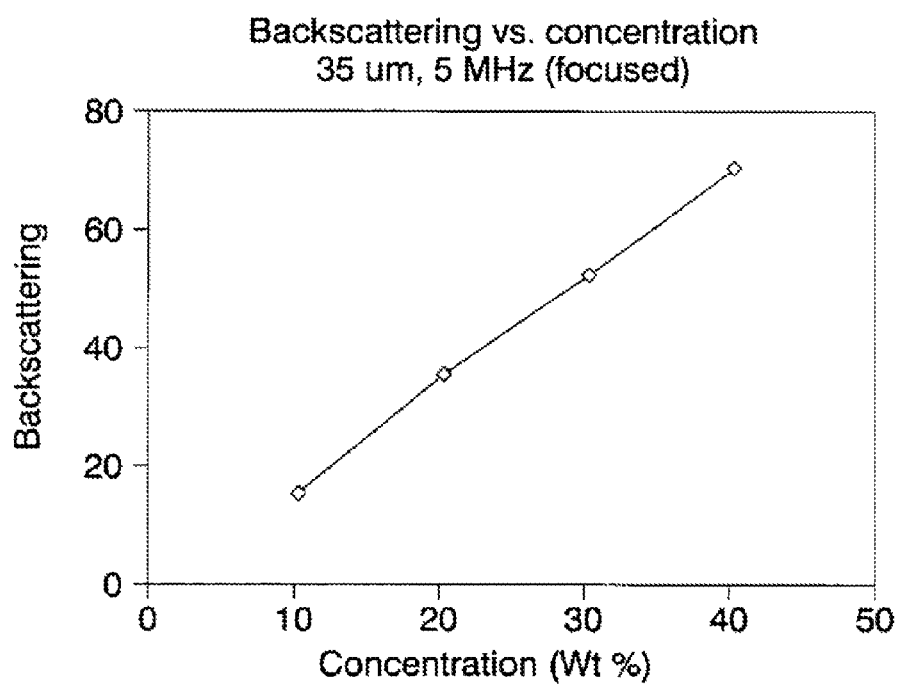
FIGS. 9A and 9B are representative plots of backscattering signals as a function of concentration for suspensions with 35 μm and 70 μm glass spheres, respectively.
Figure 9B:
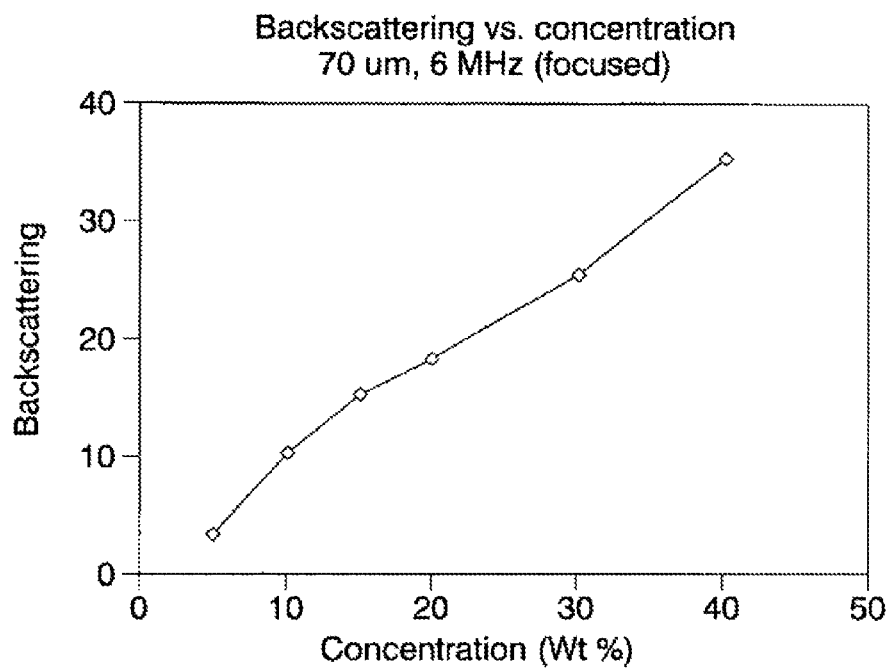

Once the frequency response from a gated region of backscattering measurements has been determined, the backscattering at a specific frequency can be plotted as a function of concentration as shown in FIGS. 9A and 9B. In these examples, the backscattering is shown to increase linearly with respect to concentration for the 35 μm glass spheres, and shown to increase almost linearly with respect to concentration for the 70 μm glass spheres. (The y-axis units of FIGS. 9A and 9B are arbitrary units.) This linear relationship with slurry concentration contrasts with the attenuation, which deviated from a linear response at high concentration due to particle-particle interactions.

Figure 6B:
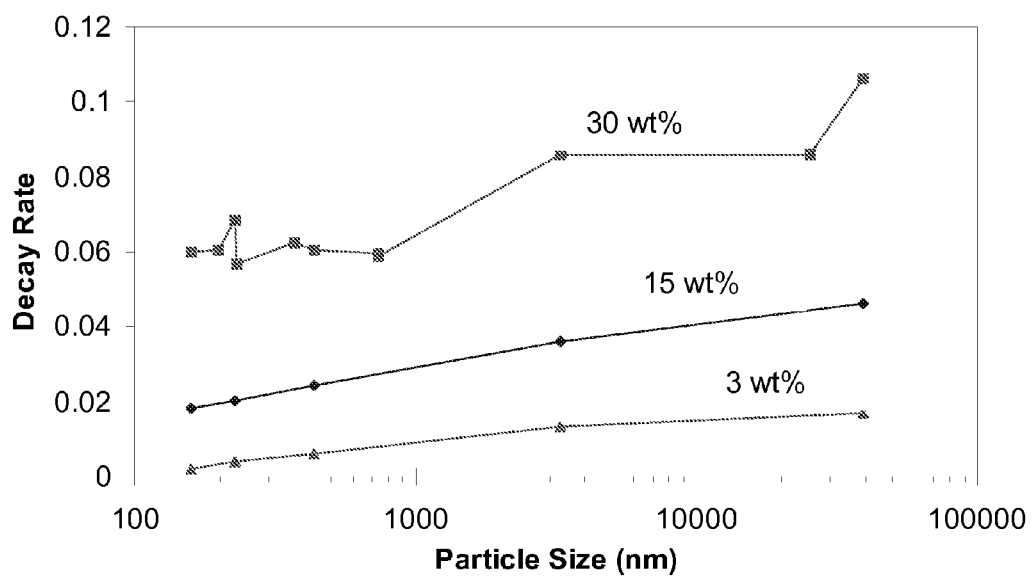
FIG. 6B is a representative plot of the decay rates of backscattering signals in slurries with three different concentrations (3 wt %, 15 wt % and 30 wt %) plotted as a function of particle size.

FIG. 6B shows an example of the decay rates of backscattering signals in slurries with three different concentrations (3 wt %, 15 wt % and 30 wt %) plotted as a function of particle size. The deviation in the 30 wt % signal at low particle size is likely due to agglomeration. This has also been detected using optical techniques and is likely not an anomaly.

Figure 1B:
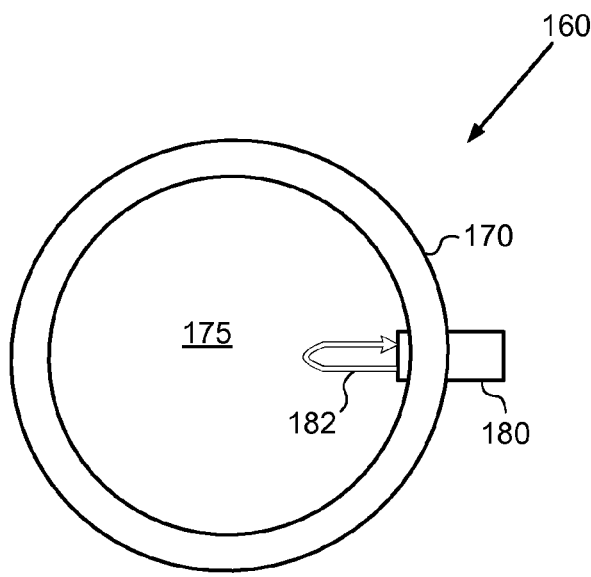

Turning to FIG. 1B, an alternative system 160 for measuring backscattered signals in solid-liquid suspensions is shown. The system 160 comprises a cylindrical container 170, which may be made of Teflon or a similar, suitable material, and which contains a suspension 175. The system has one transducer 180, which transmits an ultrasonic wave in the suspension 175. Transducer 180 also functions as a receiver to measure the backscattered signal. Other embodiments may include a reflector (not shown). In some embodiments, the transducer 180 is a focused transducer configured to measure the amplitude of a signal in a focal zone. In other embodiments, the transducer 180 is a planar transducer configured to measure the decay of backscattered energy throughout a given section of a container, e.g., throughout approximately the entire depth of the container.

The single-transducer approach of the system of FIG. 1B has some potential advantages. For example, there is no need to ensure alignment of the transducer 180 with another transducer. The design may also allow for larger propagation paths which are less likely to be clogged by the sample.

Figure 2:
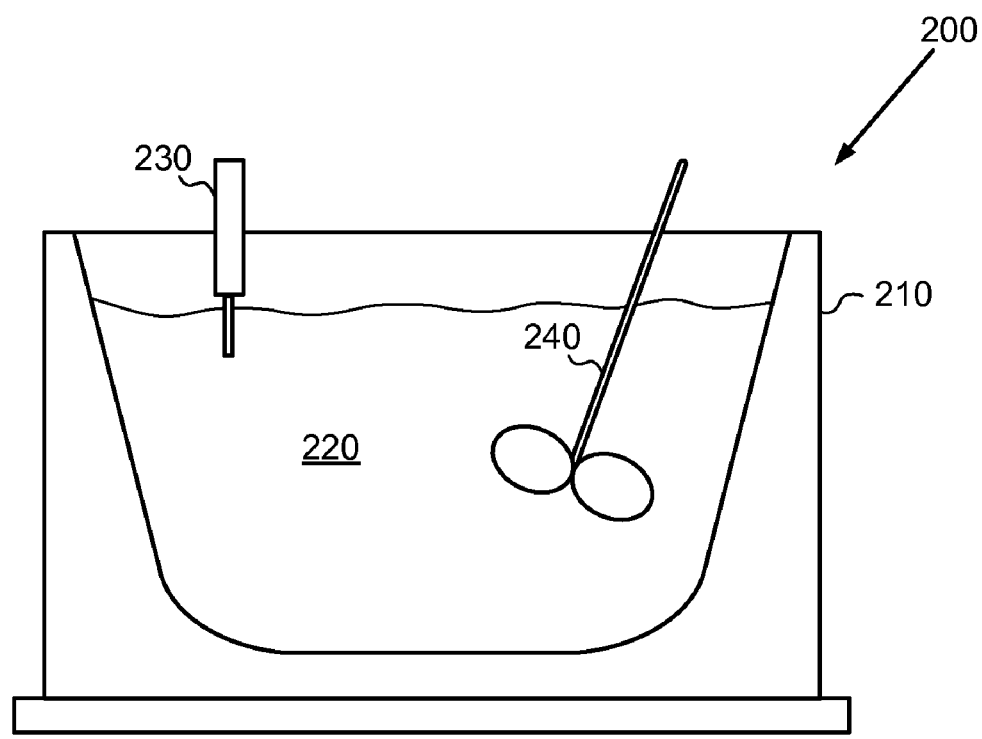
FIG. 2 is a side diagrammatic view of a container for performing diffuse field measurements on suspensions.

FIG. 2 shows a system 200 for measuring the energy loss of a diffuse field in a suspension. The system 200 comprises a container 210 (possibly made of a material that minimizes energy loss, such as foam or suspended plastic bag) with a suspension 220. A pulser (possibly a Ritec SP-801 pulser, not shown) and a receiver (possibly a Ritec BR-640 receiver, not shown) drive a pinducer 230 or other immersion transducer, planar or focused, (such as those manufactured by Valpey-Fisher) with a nominal diameter of about 1 mm. The pinducer 230 is driven in pulse-echo and pitch catch mode to measure the diffuse field signals. In one implementation, the pulser sent a 1 MHz, 400 V square wave pulse to the pinducer 230 with a 25 Hz repetition rate. A mixer 240 agitated the suspension 220 to help maintain uniformity. A diplexer was set at a damping of 1300 Ohms and a low-frequency cutoff of 30 kHz. The gain of the receiver was set to 56 dB with a high input impedance and a bandpass filter between 500 kHz and 3 MHz. Five ultrasonic waveforms were averaged and captured at a sampling rate of 50 MHz.

Figure 10A:
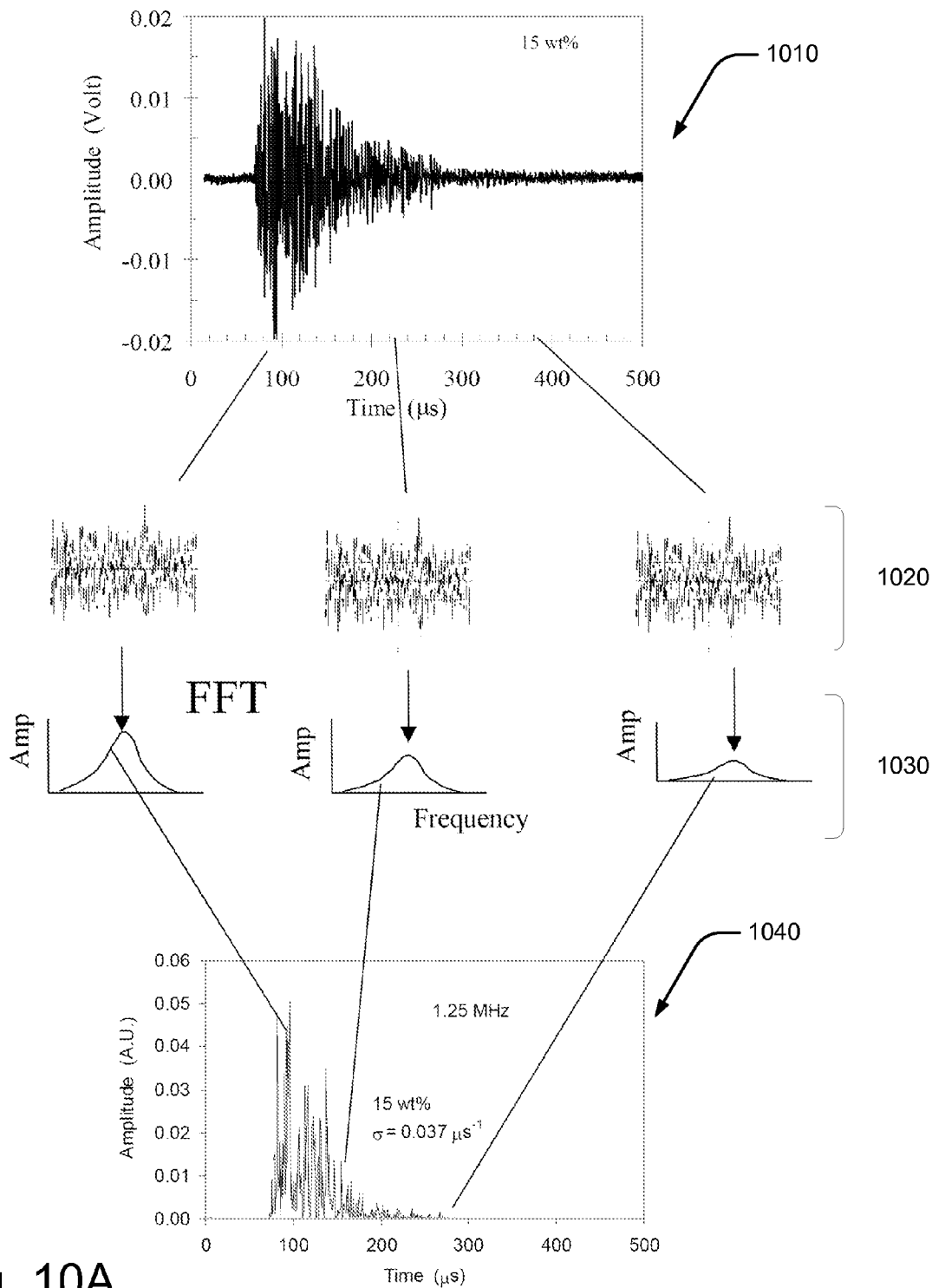
FIG. 10A shows a process of performing a time-frequency analysis of an ultrasonic waveform to determine the attenuating effect of a slurry.
Figure 10B:
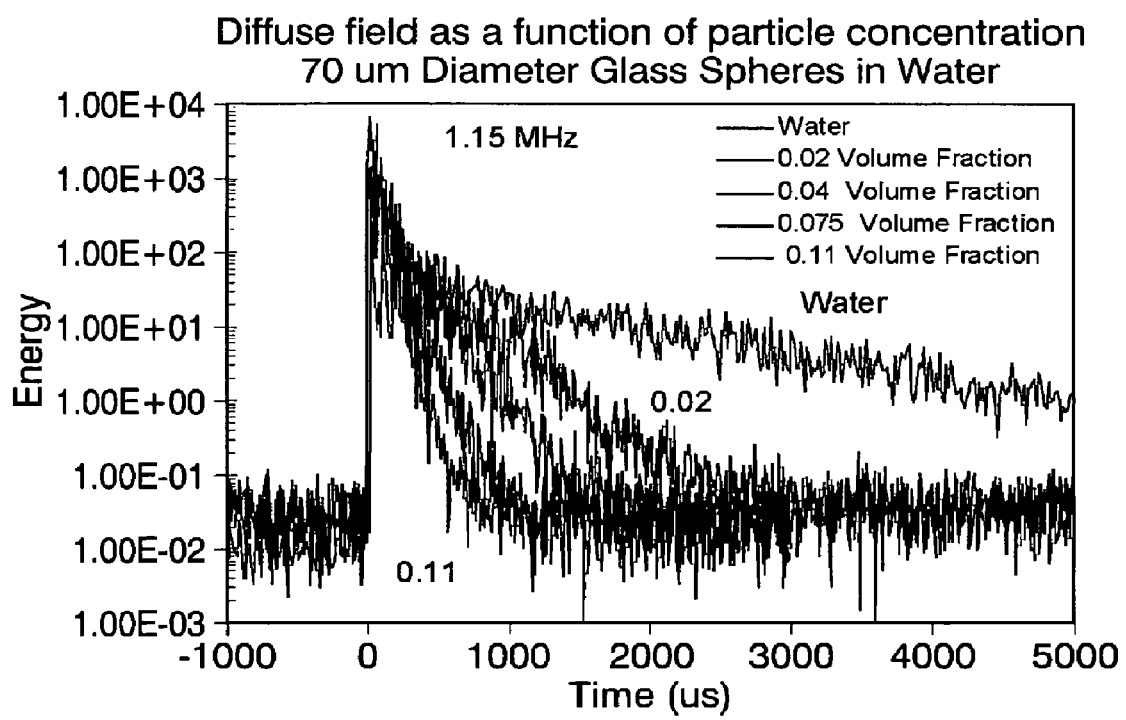
FIG. 10B is a representative plot of diffuse field measurements as a function of particle concentration.

The attenuating effect of the 15 wt % slurry was obtained from the decay of the diffuse field by performing a time-frequency analysis on the ultrasonic waveform. The process of time-frequency analysis is exemplified in FIG. 10. First, the ultrasonic waveform shown in graph 1010 was segmented into several 0.5 μs-time windows ($\Delta t$) 1020. (Note that the windows 1020 appearing in FIG. 10 are example waveforms and not necessarily waveforms of actual data.) For the different time windows 1020, a Fourier transform was performed to produce an amplitude Amp in the window with respect to frequency (1030). The square of the amplitude Amp was then integrated over $\Delta f$=250 kHz windows centered at $f_0$ according to the equation:

$$\text{Amplitude}(f, t) \propto \int_{f_0 - \frac{\Delta f}{2}}^{f_0 + \frac{\Delta f}{2}} Amp^2(f, \Delta t) df \tag{2}$$

Using this equation, graph 1040 was produced, which shows the decay analysis for a frequency $f$=1.25 MHz±250 kHz, and with a decay rate $\sigma$=0.037 μs$^{-1}$. The size of the time window and frequency bin were chosen to provide the best results for this particular slurry. See, e.g., Weaver et al., "Diffusion of ultrasound in a glass bead slurry," *J. of the Optical Soc. of Am.*, 97:2094-2102, 1995. The result was a quantity proportional to the acoustic energy as a function of frequency and time, where the frequency and time values were taken to be the center of the windows (see FIG. 10A). From the time dependence, a frequency dependent exponential decay constant of the energy was determined by fitting the data to an exponential:

$$\text{Energy}(f) = E_0 e^{-\sigma(f) t} \tag{3}$$

where $E_0$ is the amplitude at the peak of the energy, $\sigma$ is a decay rate as a function of frequency, and $t$ is the time. The results for various concentrations, recorded for $f$=1.15 MHz, appear in FIG. 10B and show that the diffuse field decayed more rapidly as the concentration increased, implying more energy loss due to damping.

Some commercial measurement devices rely on a model similar to the one described in Allegra et al., "Attenuation of sound in suspensions and emulsions: theory and experiments," *J. of the Acoust. Soc. of Am.*, 51(5):1545-1564, 1972, which considers single scattering and absorption. However, some commercial devices measure the through-transmitted attenuation, which can be influenced by multiple scattering and particle-particle interactions that are not included in the model of Allegra et al. Thus the commercial devices which rely on the model of Allegra et al. are basing their determination of particle size on invalid assumptions at higher concentrations (e.g., greater than 15 wt %).

As noted above with respect to FIG. 4B, the through-transmission attenuation of a signal, as a function of concentration at fixed frequency, deviates from an expected linear relationship above approximately 10 wt %. This deviation is likely an indication of the importance of particle-particle interactions and multiple scattering on the attenuation. The backscattering amplitude can provide a generally linear response at higher concentrations (e.g., 10 wt % or greater), as shown in FIGS. 9A and 9B. These results can suggest that backscattering measurements can be utilized to more accurately determine the concentration of slurries with similar higher concentrations. A further comparison of through-transmission attenuation measurements backscattering measurements can be seen by comparing the through-transmission attenuation as a function of particle size, as shown in FIG. 6A, with the decay rate of the backscattering measurements as shown in FIG. 6B. At 30 wt %, the through-transmission attenuation measurement shows unpredictable fluctuations. However, the backscattering measurement decay rate can more reliably indicate the particle size over lower and higher concentrations. These backscattering amplitude and decay rate data can be used as calibration data to determine the particle size and concentration of high solids-loading slurries.

Unified Comparison of Properties of a Suspension

Comparing and combining measurements of properties of a solid-liquid suspension can allow for a better understanding of the contributions of one or more energy loss mechanisms to energy loss of an ultrasonic field. Additionally, it can help indicate the most appropriate property (or properties) to model for describing the suspension.

Experimental results show that the attenuation of the through-transmitted signal is dominated by particle-particle interactions, scattering and absorption. The decay of the backscattered signal, however, is dominated by single scattering and absorption, and the diffuse field decay rate is affected by absorption only.

Mathematically, the relationships shown in Table 1 (i.e., measurements and their respective loss mechanisms) may be described by equations 4-6.

$$\alpha_{Through\_transmission}(f) = \alpha_{Multiple\_scattering}(f) + \alpha_{Single\_scattering}(f) + \alpha_{Absorption}(f) \quad (4)$$

$$\alpha_{Backscattering\_decay}(f) = \alpha_{Single\_scattering}(f) + \alpha_{Absorption}(f) \quad (5)$$

$$\alpha_{Diffuse\_field\_decay}(f) = \alpha_{Absorption}(f) \quad (6)$$

For these equations, $\alpha_{Through\_transmission}$ corresponds to the attenuation of a through-transmitted signal, $\alpha_{Backscattering\_decay}$ corresponds to the attenuation of a backscattered signal, and $\alpha_{Diffuse\_field\_decay}$ is the attenuation of a diffuse field signal. $\alpha_{Multiple\_scattering}$ is the attenuation caused by the multiple scattering loss mechanism; $\alpha_{Single\_scattering}$ is the attenuation caused by the single scattering loss mechanism; and $\alpha_{Absorption}$ is the attenuation caused by the absorption loss mechanism.

Equations 4-6 may be rewritten to express the individual loss mechanisms:

$$\alpha_{Multiple\_scattering}(f) = \alpha_{Through\_transmission}(f) - \alpha_{Backscattering\_decay}(f) \quad (7)$$

$$\alpha_{Single\_scattering}(f) = \alpha_{Backscattering\_decay}(f) - \alpha_{Diffuse\_field\_decay}(f) \quad (8)$$

$$\alpha_{Absorption}(f) = \alpha_{Diffuse\_field\_decay}(f) \quad (9)$$

A value for $\alpha_{Through\_transmission}$ can be measured directly, as described above. The attenuation of the backscattered signal may be calculated as $$\alpha(f)_{BS} = \frac{\sigma_{BS}(f)}{2v} \quad (10)$$

where $f$ is the frequency of the ultrasonic signal, $v$ is the speed of sound in the suspension, and $\sigma_{BS}(f)$ is the decay rate function. The attenuation of the diffuse field signal may be calculated as $$\alpha(f)_{DF} = \frac{\sigma_{DF}(f)}{2v} \quad (11)$$

where $f$ is the frequency of the ultrasonic signal, $v$ is the speed of sound in the suspension, and $\sigma_{DF}(f)$ is the decay rate function. Decay rate functions in general are known in the art. See, e.g., Weaver et al. From equations 7-9, the attenuation mechanisms can be separated, allowing for direct comparison of the mechanisms, selection of an appropriate theory, and for use of the mechanisms in determining particle size, concentration and density of slurries.

Figure 11A:
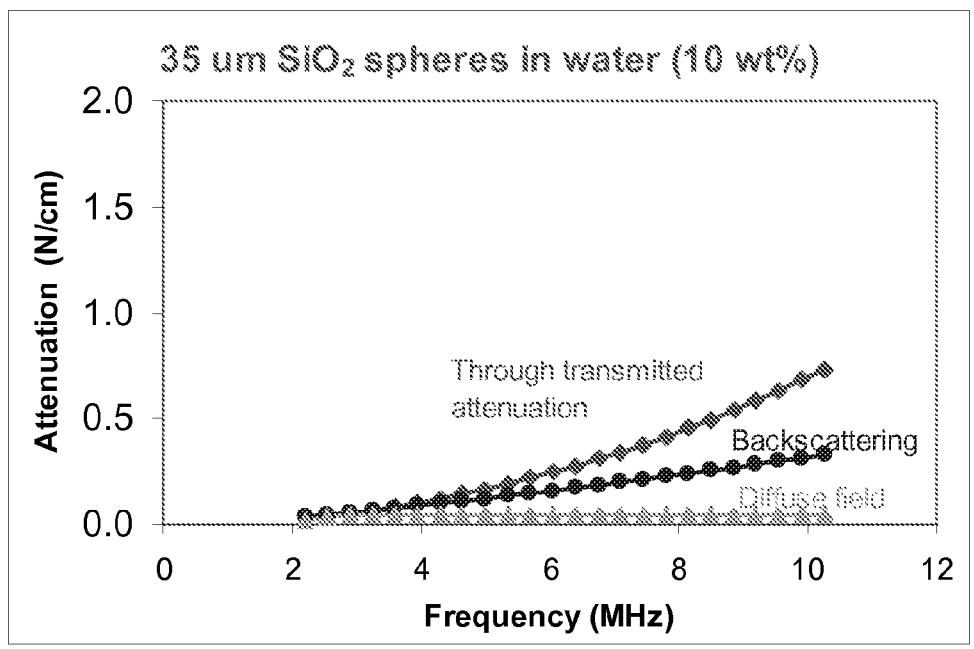
FIGS. 11A and 11B are representative plots of three suspension properties over a frequency range for slurries with 35 μm and 70 μm glass ($SiO_2$) spheres, respectively.
Figure 11B:
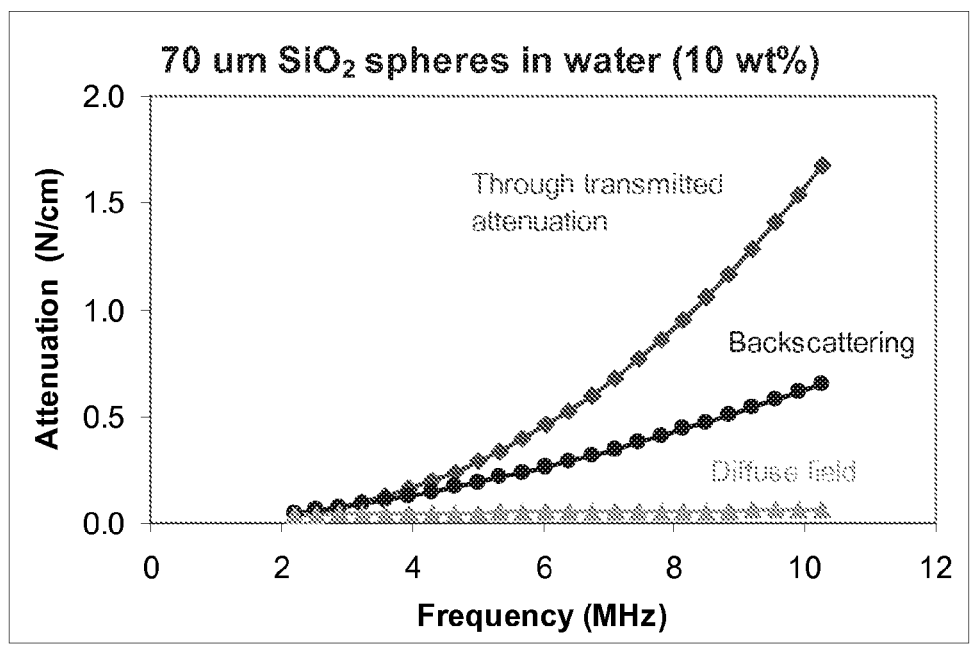

FIGS. 11A and 11B show the attenuation of through-transmitted attenuation, backscattering, and diffuse field measurements over a frequency range for slurries with 35 μm and 70 μm glass (SiO$_2$) spheres, respectively. The attenuation for each measurement is shown in nepers per centimeter of travel distance through the sample. As these figures show, at lower frequencies the attenuations of the three measurements are similar in value, indicating that they are sensitive to the same loss mechanisms at these frequencies. At higher frequencies (e.g., 10 MHz), the attenuation of the through-transmitted attenuation measurement is several times that of the attenuation of the backscattering measurement, which itself is several times that of the attenuation of the diffuse field measurement. This can be understood by considering the interrelationship between the attenuation, backscattering, and diffuse field measurements with respect to particle size and frequency. More specifically, as the product of the particle size and frequency (i.e., kR) increases, the contributions from single and multiple scattering become more dominant than the absorption contribution. This relationship also explains the notable differences between attenuations for through-transmitted attenuation and backscattering attenuation measurements for the slurry with 35 μm spheres (FIG. 11A) and the corresponding measurements for the slurry with 70 μm spheres (FIG. 11B).

Figure 12A:
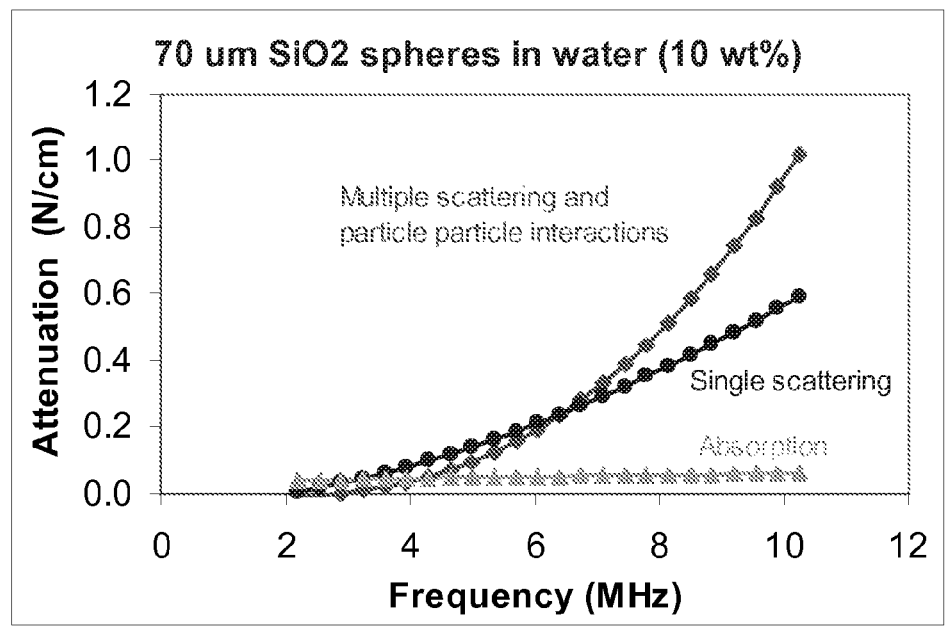
FIG. 12A is a representative plot of loss mechanism measurements taken in a 10 wt % slurry of 70 μm glass spheres in water.
Figure 12B:
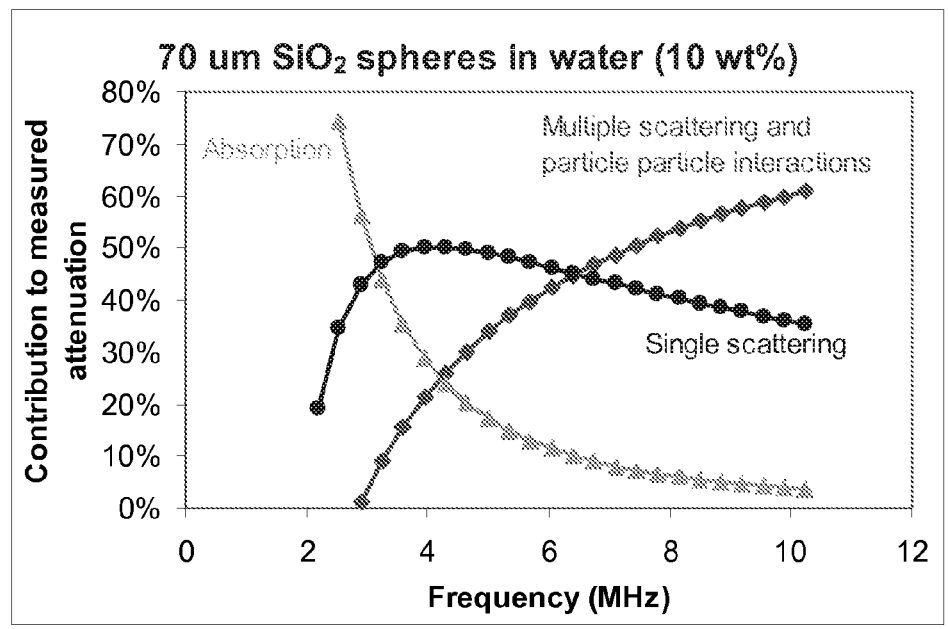
FIG. 12B is a representative plot of the contributions of individual loss mechanisms to a measured attenuation for the slurry of FIG. 12A.

Measurements such as those shown in FIGS. 11A and 11B can be converted into loss mechanism measurements, using the equations described above. For example, the measurements of FIG. 11B, taken in a 10 wt % slurry of 70 μm glass spheres in water, produce the loss mechanism measurements shown in FIG. 12A. Additionally, these loss mechanism measurements may be expressed in terms of their contribution to overall measured attenuation of a signal. FIG. 12B shows the data of FIG. 12A in such terms, illustrating how the contributions of the different loss mechanisms change with respect to frequency.

Figure 13A:
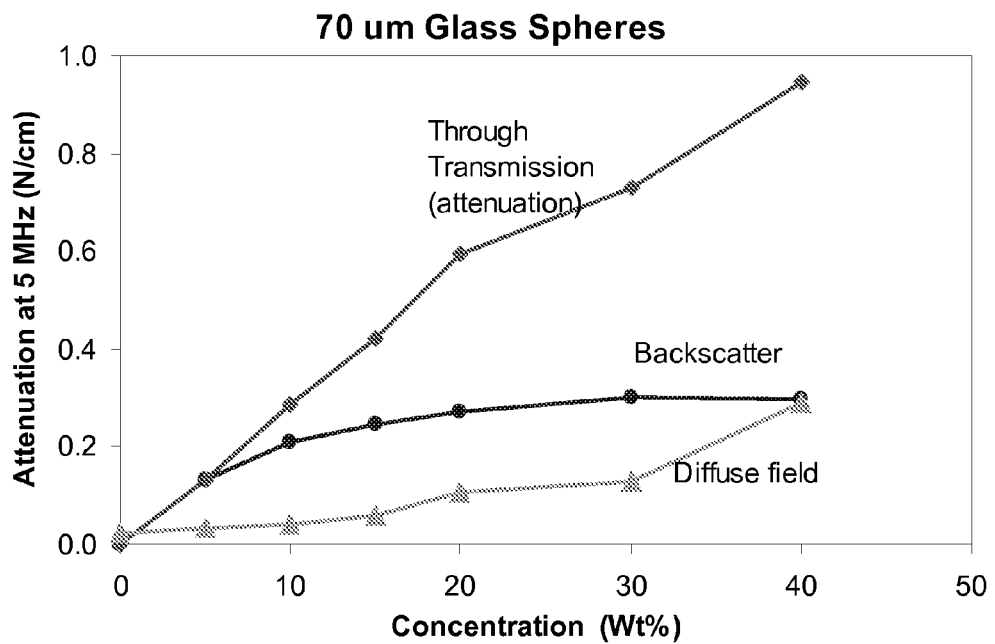
FIG. 13A is a representative plot of measurements of suspension properties for suspensions of varying concentrations.
Figure 13B:
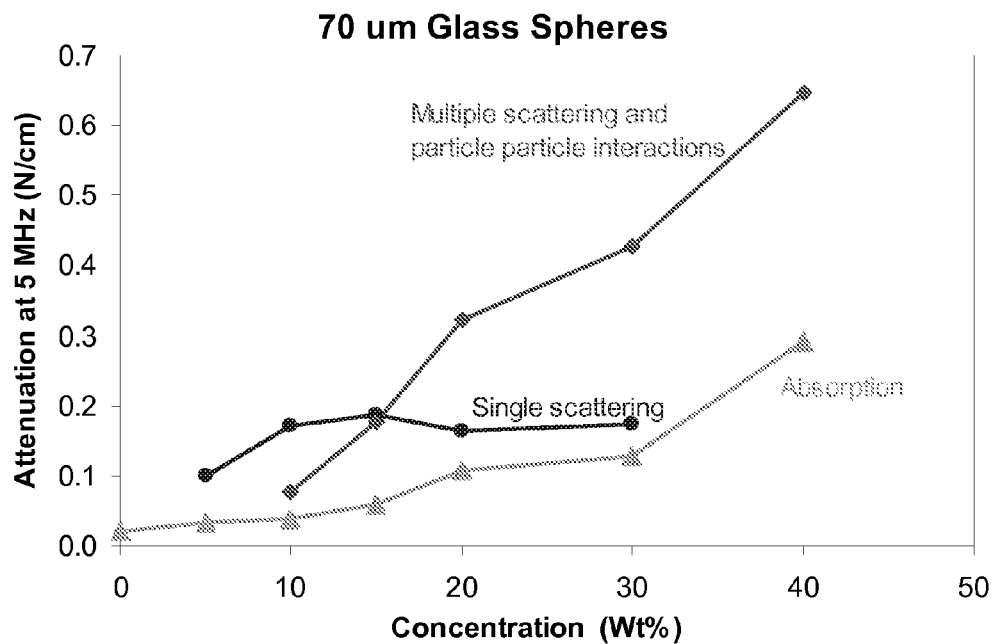
FIG. 13B is a representative plot of attenuation contributed by various loss mechanisms for the suspension property measurements of FIG. 13A.
Figure 13C:
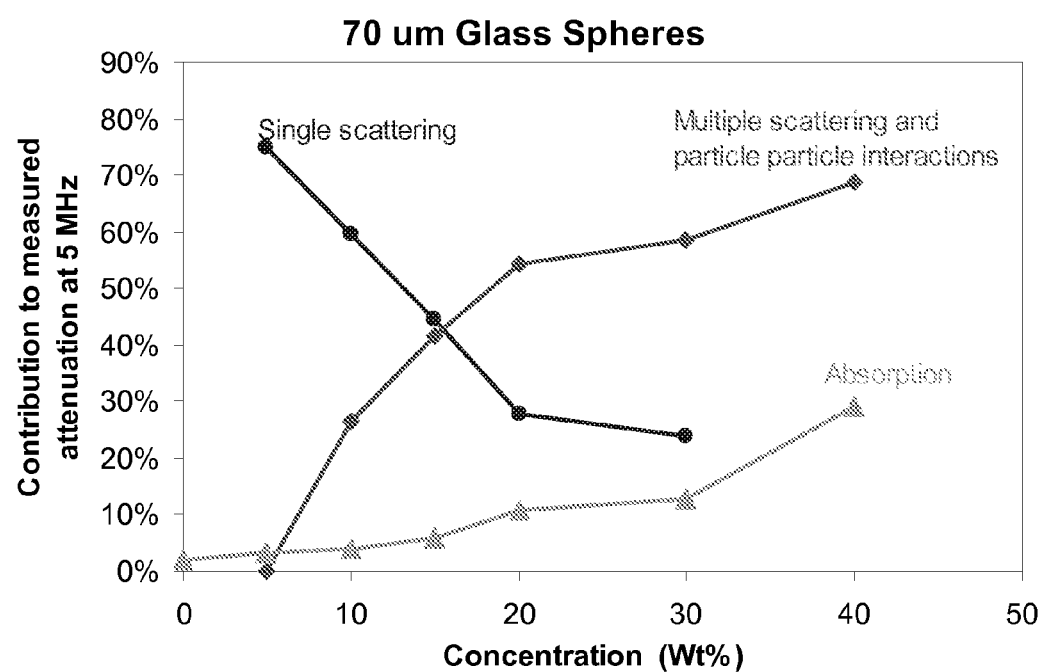
FIG. 13C is a representative plot of the contributions of individual loss mechanisms to a measured attenuation for the slurry of FIG. 13A.

Similar measurements may also be taken over a range of slurry concentrations. For example, FIG. 13A shows attenuation measurements for through-transmission, backscatter and diffuse field signals measured in a slurry containing 70

μm glass spheres in water, with concentrations ranging from 0 to 40 wt %. FIG. 13B shows these measurements, converted using equations 7-9, in terms of loss mechanisms. FIG. 13C shows the contributions of these mechanisms to the overall attenuation of a signal over a range of slurry concentrations.

In another embodiment, a unified way to compare the quantities of attenuation, backscattering and diffuse field is to calculate a degree of energy loss for one or more of the quantities. This may be done using the following equations, which define an inverse Q factor ($Q^{-1}$) which represents the degree of energy loss:

$$Q^{-1}_{Atten}(f) = \frac{v\alpha(f)}{\pi f} \quad (12)$$

$$Q^{-1}_{BS}(f) = \frac{\sigma_{BS}(f)}{2\pi f} \quad (13)$$

$$Q^{-1}_{DF}(f) = \frac{\sigma_{DF}(f)}{2\pi f} \quad (14)$$

In equations 12-14, "Atten," "BS" and "DF" designate the inverse Q factor for through-transmission attenuation, backscattering, and diffuse field measurements, respectively. The speed of sound in the slurry is represented by $v$, $f$ represents the frequency, $\sigma$ is the decay function of the ultrasonic field, and $\alpha$ is the through-transmitted attenuation as a function of frequency.

Characterizing Suspensions Using Unified Comparison

As described above and shown in the accompanying figures, measurements in solid-liquid suspensions can be dominated by different loss mechanisms at different frequencies and particle concentrations. Being able to determine and compare these mechanisms can allow a user or a measurement device to select a model that is appropriate for the loss mechanisms which contribute to the attenuation of a signal. Using an appropriate model can, in turn, allow for determining suspension properties such as particle size, concentration, and density.

Figure 14:
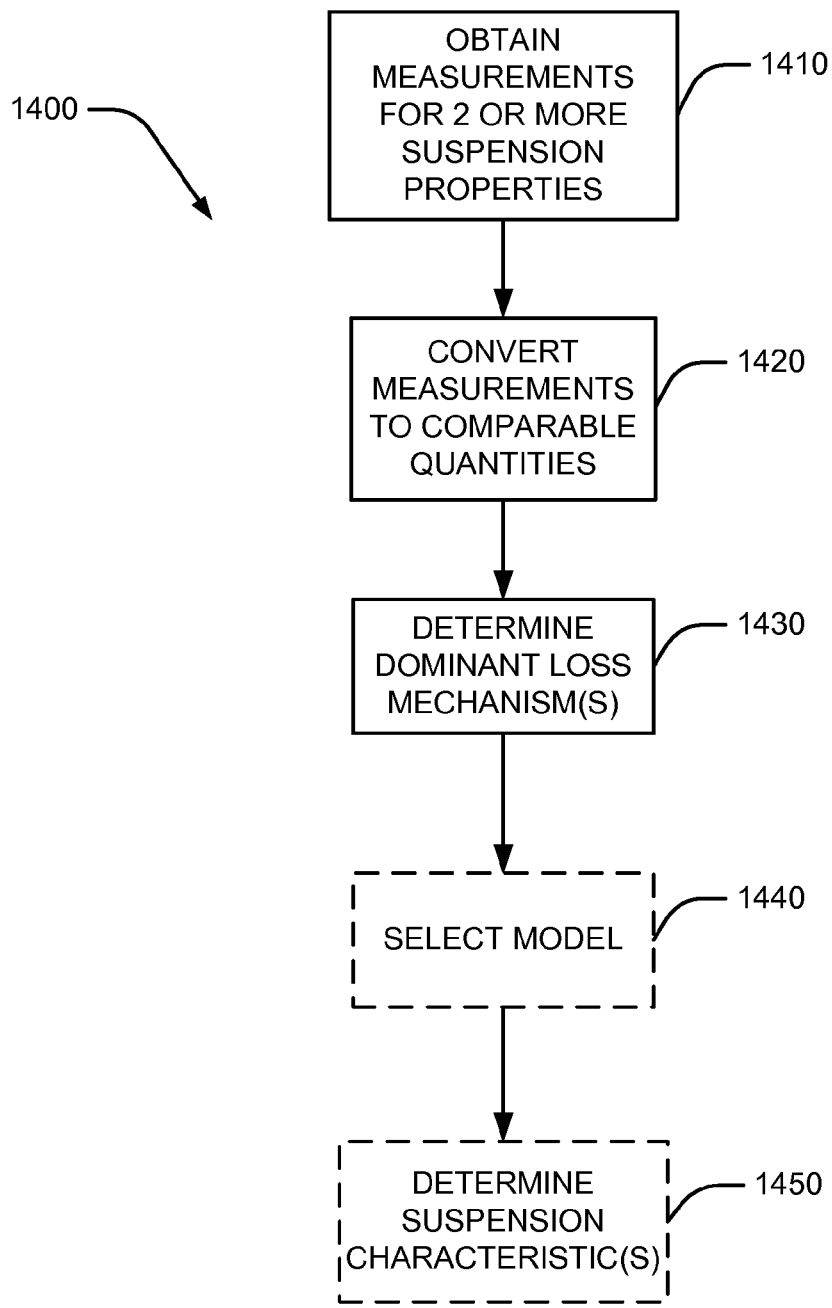
FIG. 14 is a flowchart outlining a method of characterizing a solid liquid suspension.

FIG. 14 shows a method 1400 of characterizing a solid liquid suspension. In step 1410, property measurements for two or more suspension properties are obtained, perhaps using one or more of the methods and apparatus described above. The measurements are converted to comparable quantities (step 1420) using, for example, the above equations. The comparable quantities may be in terms of attenuation or in terms of degree of energy loss, though attenuation is preferred. The converted measurements from the different ultrasonic properties are used to determine one or more dominant loss mechanisms (step 1430). In this context, a first loss mechanism is "dominant" relative to a second loss mechanism if the first loss mechanism causes a higher percentage of the total attenuation of the signal than the second loss mechanism. In further embodiments, based on this determination, an appropriate model is selected (step 1440). For example, if single scattering is determined to be a dominant loss mechanism, then the model described by Allegra et al. can be selected. As another example, if multiple scattering is determined to be a dominant loss mechanism, then the model described by Varadan et al., "A propagator model for scattering of acoustic waves by bubbles in water," *J. of the Acoust. Soc. of Am.*, 78(5):1879, 1985, can be selected. As a further example, if absorption is determined to be a dominant loss mechanism, then the model described by Kytomaa, H. K., "Theory of sound propagation in suspensions: a guide to particle size and concentration characterization," *Powder Tech.*, 82:115-121, 1991, can be selected. It should be noted that the models mentioned here are merely exemplary, and that additional models can be selected as appropriate.

Using the selected model, one or more suspension properties (e.g., particle size, concentration, and density) can be determined (step 1450) with methods that are known in the art.

In one example, it is assumed that the measurements for through-transmission, backscatter and diffuse field are obtained for a sample slurry and used to calculate $\alpha_{Through\_transmission}$, $\alpha_{Backscattering\_decay}$, and $\alpha_{Diffuse\_field\_decay}$, respectively. These figures are then used to determine the loss mechanism terms $\alpha_{Multiple\_scattering}$, $\alpha_{Single\_scattering}$ and $\alpha_{Absorption}$. In this example, the rounded values for these terms are as shown in Table 3.

TABLE 3

| Loss mechanism term | Attenuation (N/cm) | Percentage of total attenuation |
|---|---|---|
| $\alpha_{Multiple}$—scattering | 0.5 | 50% |
| $\alpha_{Single}$—scattering | 0.4 | 42% |
| $\alpha_{Absorption}$ | 0.05 | 5% |

From the figures in Table 3, it can be seen that absorption makes a relatively small contribution to the total measured attenuation of the ultrasonic signal, while single and multiple scattering make more significant contributions. Accordingly, a model that accounts mostly or exclusively for absorption and single scattering (but not for multiple scattering) would not account for a loss mechanism responsible for 50% of the total signal attenuation, and property characteristics produced using that model can be expected to have limited accuracy. Similarly, a model accounting for both multiple scattering and single scattering loss mechanisms (but not accounting for absorption) could produce relatively accurate property characteristics, as multiple scattering and single scattering are the dominant loss mechanisms in this example.

Exemplary Implementation System

Figure 15:
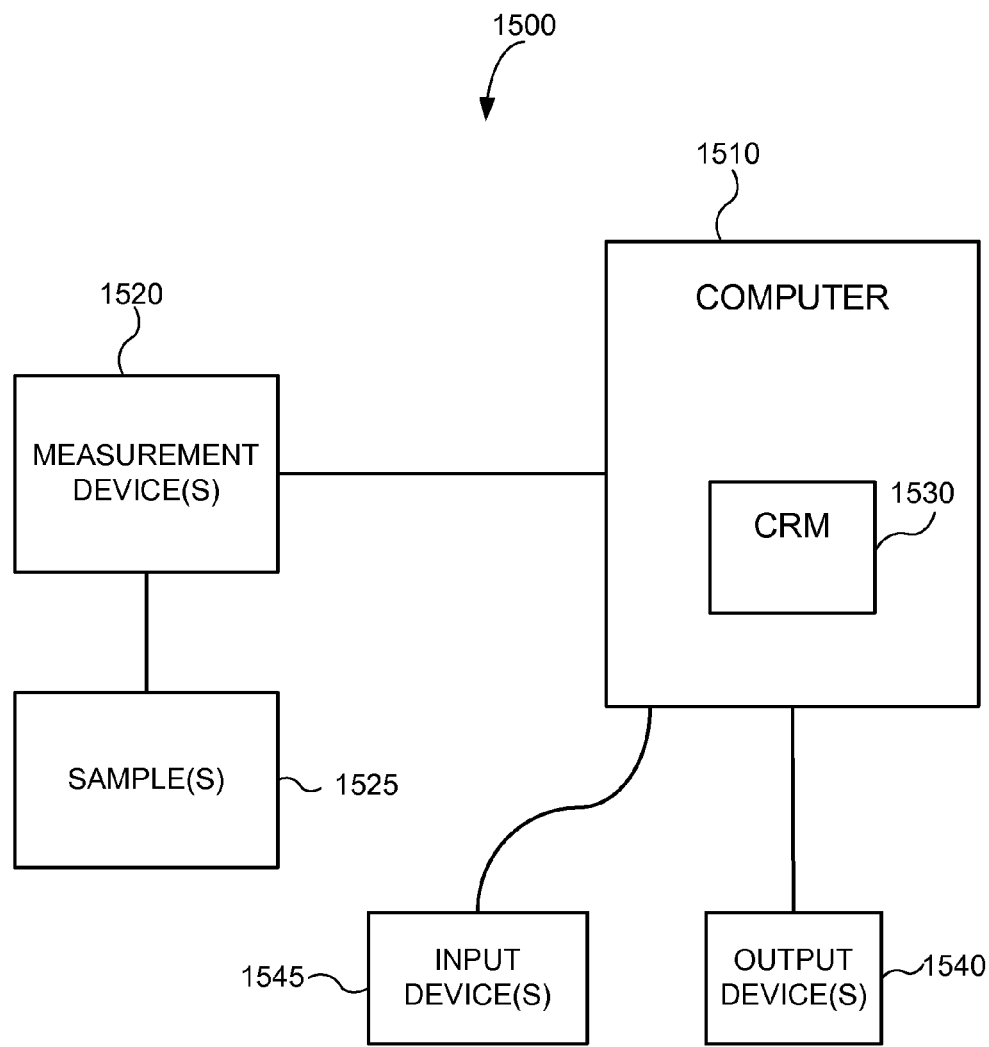
FIG. 15 is a block diagram of an exemplary system for implementing the method of FIG. 14.

FIG. 15 depicts one possible system 1500 for implementing the technologies described above. The system 1500 comprises a conventional computer 1510 (such as a personal computer, a laptop, a server, a mainframe, and other varieties of computers) that is configured to receive data from one or more ultrasonic measurement devices 1520 analyzing one or more samples 1525. The measurement devices may be similar to those depicted in FIGS. 1A, 1B and 2, or they may be other devices known in the art that are capable of measuring properties of solid-liquid suspensions.

The computer 1510 contains computer-readable media (CRM) 1530 that may include a hard disk drive, a magnetic disk drive, e.g., to read from or write to a removable disk, an optical disk drive, e.g., for reading a CD-ROM disk or to read from or write to other optical media, RAM, ROM, magnetic cassettes, flash memory cards, digital video disks, Bernoulli cartridges, and other similar devices as are known in the art. The CRM 1530 contains instructions that cause the computer 1510 to receive measurement data from the measurement devices 1520, and to perform the method 1400 of FIG. 14. The CRM 1530 may also contain statistical software or other software for analyzing the results of the method 1400.

The computer 1510 may receive information through input devices 1545 and may display results on output devices 1540. The input devices may comprise a keyboard and pointing device, such as a mouse. Output devices may comprise a monitor or other type of display device, as well as speakers and printers. The CRM 1530 may contain instructions that cause the computer 1510 to display on the output devices 1540 at least some calculations and results of the method 1400. For example, after analyzing the samples 1525 and performing the method 1400, the computer 1510 may indicate to a user the percentage of total attenuation for one or more loss mechanisms of the samples. The computer 1510 may also be configured to recommend one or more models that may be appropriate for determining properties of the samples 1525 based on the results of the method 1400. The recommendations may be based in part on parameters provided by a user, perhaps through input devices 1545. For example, the user may indicate what models are available, or what divergence thresholds should be applied at step 1440 of method 1400. Results obtained by the method 1400 can be stored in the CRM 1530.

In view of the many possible embodiments to which the principles of the disclosed technologies may be applied, it should be recognized that the illustrated embodiments are only preferred examples of the technologies and should not be taken as limiting the scope of the invention. Rather, the scope of the invention is defined by the following claims. I therefore claim as my invention all that comes within the scope and spirit of these claims.

I claim:

1. A method of characterizing a solid liquid suspension, the method comprising:
    obtaining two or more property measurements for the suspension using an ultrasonic field;
    converting the obtained two or more property measurements to comparable quantities, wherein the comparable quantities allow at least two of the obtained two or more property measurements to be compared with each other;
    determining, according to the comparable quantities, that a first loss mechanism for the suspension caused a higher percentage of an energy loss or attenuation of the ultrasonic field in the suspension than a second loss mechanism for the suspension, the first and second loss mechanisms each comprising a different interaction between the suspension and the ultrasonic field; and
    selecting from a plurality of models, according to the determination made according to the comparable quantities, a model for characterizing the suspension, the selected model accounting for one or more effects of the first loss mechanism on the ultrasonic field in the suspension.

2. The method of claim 1, further comprising:
    determining one or more characteristics of the suspension by evaluating one or more of the property measurements according to the selected model.

3. The method of claim 2, wherein at least one of the following characteristics of the suspension is determined: particle size, concentration, and density.

4. The method of claim 1, wherein determining, according to the comparable quantities, that the first loss mechanism for the suspension caused the higher percentage of the energy loss or attenuation of the ultrasonic field in the suspension comprises determining a contribution to a total measured attenuation for one or more loss mechanism terms.

5. The method of claim 1, wherein the one or more loss mechanisms are selected from the group: multiple scattering, single scattering, and absorption.

6. The method of claim 1, wherein converting the property measurements to comparable quantities comprises determining an attenuation of one or more of the property measurements.

7. The method of claim 6, wherein converting the property measurements further comprises calculating an attenuation due to a loss mechanism.

8. The method of claim 7, wherein the loss mechanism is multiple scattering, and wherein the attenuation due to the loss mechanism is calculated as a difference of an attenuation of a through-transmitted signal and an attenuation of a backscattered signal.

9. The method of claim 7, wherein the loss mechanism is single scattering, and wherein the attenuation due to the loss mechanism is calculated as a difference of an attenuation of a backscattered signal and an attenuation of a diffuse field signal.

10. The method of claim 7, wherein the loss mechanism is absorption, and wherein the attenuation due to the loss mechanism is calculated as equal to an attenuation of a diffuse field signal.

11. The method of claim 6, wherein the property measurements comprise a backscattering measurement and determining the attenuation of one or more of the property measurements comprises determining an attenuation $\alpha(f)_{BS}$ according to an equation:

$$\alpha(f)_{BS} = \frac{\sigma_{BS}(f)}{2v},$$

wherein $f$ is the frequency of the ultrasonic signal, $\sigma_{BS}(f)$ is the decay rate function, and $v$ is the speed of sound in the suspension.

12. The method of claim 6, wherein the property measurements comprise a diffuse field measurement and determining the attenuation of one or more of the property measurements comprises determining an attenuation $\alpha(f)_{DF}$ according to an equation:

$$\alpha(f)_{DF} = \frac{\sigma_{DF}(f)}{2v},$$

wherein $f$ is the frequency of the ultrasonic signal, $\sigma_{DF}(f)$ is the decay rate function, and $v$ is the speed of sound in the suspension.

13. The method of claim 1, wherein the solid liquid suspension has a solid concentration between approximately 0 wt % and approximately 50 wt %.

14. The method of claim 1, wherein the solid liquid suspension has a solid concentration greater than approximately 10 wt %.

15. The method of claim 1, wherein converting the obtained two or more property measurements to comparable quantities comprises calculating a degree of energy loss for the obtained two or more property measurements.

16. The method of claim 15, wherein the property measurements comprise a through-transmission attenuation measurement, and wherein calculating the degree of energy loss for the obtained two or more property measurements comprises calculating a degree of energy loss $Q_{Atten}^{-1}(f)$ for the through-transmission attenuation measurement according to an equation $$Q_{Atten}^{-1}(f) = \frac{v\alpha(f)}{\pi f}$$

wherein v represents the speed of sound in the suspension, $f$ represents a frequency of the ultrasonic field, and $\alpha(f)$ represents the through-transmitted attenuation of the ultrasonic field as a function of the frequency.

17. The method of claim 15, wherein the property measurements comprise a backscattering measurement, and wherein calculating the degree of energy loss for the obtained two or more property measurements comprises calculating a degree of energy loss $Q_{BS}^{-1}(f)$ for the backscattering measurement according to an equation $$Q_{BS}^{-1}(f) = \frac{\sigma_{BS}(f)}{2\pi f}$$

wherein $f$ represents a frequency of the ultrasonic field, and $\sigma_{BS}(f)$ represents the decay function of a backscattered signal of the ultrasonic field as a function of the frequency.

18. The method of claim 15, wherein the property measurements comprise a diffuse field measurement, and wherein calculating the degree of energy loss for the obtained two or more property measurements comprises calculating a degree of energy loss $Q_{DF}^{-1}(f)$ for the diffuse field measurement according to an equation $$Q_{DF}^{-1}(f) = \frac{\sigma_{DF}(f)}{2\pi f}$$

wherein $f$ represents a frequency of the ultrasonic field, and $\sigma_{DF}(f)$ represents the decay function of a diffuse field signal of the ultrasonic field as a function of the frequency.

19. The method of claim 1, wherein the property measurements comprise attenuation, backscattering, and diffuse field.

20. A system for characterizing a solid liquid suspension, the system comprising:
    an ultrasonic measurement device; and
    a computer, wherein the computer is configured to perform a method comprising:
        receiving from the measurement device two or more property measurements for the suspension;
        converting the obtained two or more property measurements to comparable quantities, wherein the comparable quantities allow at least two of the obtained two or more property measurements to be compared with each other;
        determining, according to the comparable quantities, that a first loss mechanism for the suspension caused a higher percentage of an energy loss or attenuation of the ultrasonic field in the suspension than a second loss mechanism for the suspension, the first and second loss mechanisms each comprising a different interaction between the suspension and the ultrasonic field; and
        selecting from a plurality of models, according to the determination made according to the comparable quantities, a model for characterizing the suspension, the selected model accounting for one or more effects of the first loss mechanism on the ultrasonic field in the suspension.

21. The system of claim 20, further comprising an output device for displaying one or more results related to the method.

22. The system of claim 20, further comprising an input device for receiving one or more parameters related to the method.

23. The system of claim 20, wherein the method further comprises:
    determining one or more characteristics of the suspension by evaluating one or more of the property measurements according to the selected model.

24. The system of claim 23, wherein the determining one or more characteristics of the suspension comprises determining one or more of the following properties for the suspension: particle size, particle concentration, and suspension density.

25. A computer readable medium containing instructions that can cause a computer to execute a method, the method comprising:
    obtaining two or more property measurements for a solid liquid suspension using an ultrasonic field;
    converting the obtained two or more property measurements to comparable quantities, wherein the comparable quantities allow at least two of the obtained two or more property measurements to be compared with each other;
    determining, according to the comparable quantities, that a first loss mechanism for the suspension caused a higher percentage of an energy loss or attenuation of the ultrasonic field in the suspension than a second loss mechanism for the suspension, the first and second loss mechanisms each comprising a different interaction between the suspension and the ultrasonic field;
    selecting from a plurality of models, according to the determination made according to the comparable quantities, a model for characterizing the suspension, the selected model accounting for one or more effects of the first loss mechanism on the ultrasonic field in the suspension; and
    storing the results of the determination.

26. The computer readable medium of claim 25, wherein the method further comprises:
    determining one or more characteristics of the suspension by evaluating one or more of the property measurements according to the selected model.

27. The computer readable medium of claim 26, wherein the determining one or more characteristics of the suspension comprises determining one or more of the following properties for the suspension: particle size, particle concentration, and suspension density.

28. A method of characterizing a solid liquid suspension, the method comprising:
    obtaining two or more property measurements for the suspension using an ultrasonic field;
    determining, based at least in part on the obtained two or more property measurements, one or more attenuations of the field by individual loss mechanisms, wherein each of the one or more individual loss mechanisms comprises a different interaction between the suspension and the ultrasonic field, the one or more attenuations of the field by the one or more individual loss mechanisms being determined by one or more of a group consisting of,
        a difference of an attenuation of a through-transmitted signal and an attenuation of a backscattered signal,
        a difference of an attenuation of a backscattered signal and an attenuation of a diffuse field signal, and an equivalent of an attenuation of a diffuse field signal;
determining, according to the determined contributions, that a first of the individual loss mechanisms for the suspension caused a higher percentage of an attenuation of the ultrasonic field in the suspension than a second of the individual loss mechanisms for the suspension;
selecting from a plurality of models, according to the determination made according to the determined contributions, a model for the solid liquid suspension, the selected model accounting for one or more effects of the first of the individual loss mechanisms on the ultrasonic field in the suspension; and determining one or more characteristics of the suspension by evaluating one or more of the property measurements according to the selected model.

29. The method of claim 6, wherein the determining the attenuation of one or more of the property measurements comprises performing a time-domain calculation for at least one of the property measurements.

30. The method of claim 15, wherein the property measurements comprise an attenuation measurement.

* * * * *